(12) United States Patent
Kapur et al.

(10) Patent No.: US 9,468,666 B2
(45) Date of Patent: Oct. 18, 2016

(54) TREATMENT OF HEART FAILURE AND RELATED CONDITIONS

(75) Inventors: Navin K. Kapur, Hanover, MA (US); Richard H. Karas, Franklin, MA (US)

(73) Assignee: Tufts Medical Center, Inc., Boston, MA (US)

( * ) Notice: Subject to any disclaimer, the term of this patent is extended or adjusted under 35 U.S.C. 154(b) by 146 days.

(21) Appl. No.: 14/112,748

(22) PCT Filed: Jul. 31, 2012

(86) PCT No.: PCT/US2012/049018
§ 371 (c)(1),
(2), (4) Date: Apr. 9, 2014

(87) PCT Pub. No.: WO2013/019805
PCT Pub. Date: Feb. 7, 2013

(65) Prior Publication Data
US 2014/0234319 A1 Aug. 21, 2014

Related U.S. Application Data

(60) Provisional application No. 61/578,477, filed on Dec. 21, 2011, provisional application No. 61/513,930, filed on Aug. 1, 2011.

(51) Int. Cl.
| | |
|---|---|
| *A61K 39/395* | (2006.01) |
| *A61K 38/18* | (2006.01) |
| *A61K 38/17* | (2006.01) |
| *A61K 31/7088* | (2006.01) |
| *C07K 16/22* | (2006.01) |
| *A61K 31/713* | (2006.01) |
| *C07K 16/28* | (2006.01) |

(52) U.S. Cl.
CPC ....... *A61K 38/1841* (2013.01); *A61K 31/7088* (2013.01); *A61K 31/713* (2013.01); *A61K 38/177* (2013.01); *A61K 38/179* (2013.01); *C07K 16/22* (2013.01); *C07K 16/2896* (2013.01)

(58) Field of Classification Search
None
See application file for complete search history.

(56) References Cited

U.S. PATENT DOCUMENTS 8,221,753 B2 * 7/2012 Theuer ............... C07K 16/2896
424/130.1
2009/0170767 A1 7/2009 Karumanchi et al.
2009/0286271 A1 11/2009 Karumanchi et al.
2011/0076263 A1 3/2011 Theuer et al.
2011/0129551 A1 6/2011 Hubel et al.

FOREIGN PATENT DOCUMENTS

| CN | 103781798 A | 5/2014 |
|---|---|---|
| WO | WO-2011/088047 A1 | 7/2011 |
| WO | WO-2012/145539 A1 | 10/2012 |

OTHER PUBLICATIONS

International Search Report and Written Opinion for International Application No. PCT/US12/49018, mailed Nov. 26, 2012 (15 pages).
Extended European Search Report for 12820719.8, dated Mar. 17, 2015 (11 pages).
Kapur et al., "Reducing endoglin activity limits calcineurin and TRPC-6 expression and improves survival in a mouse model of right ventricular pressure overload," J Am Heart Assoc. 3(4):e000965 (2014) (16 pages).
Shyu et al., "Mechanism of the inhibitory effect of atorvastatin on endoglin expression induced by transforming growth factor-beta1 in cultured cardiac fibroblasts," Eur J Heart Fail. 12(13):219-226 (2010).
Jiang et al., "Abstract 4828: Effect of atorvastatin on pulmonary hypertension and lung function and remodeling in heart failure," Circulation. 118:S945 (2008).
Office Action for Chinese Patent Application No. 201280048253.5 , dated Jun. 2, 2015 (18 pages).
International Preliminary Report on Patentability for PCT/US2012/049018, issued Feb. 4, 2014 (6 pages).
Notice of Reasons for Rejection for Japanese Patent Application No. 2014-524031, mailed Apr. 25, 2016 (12 pages).
Kapur, "Osler, Weber, and Rendu: Providing insights into cardiac remodeling a century later," Hematology Reports, 9th International Hereditary Hemorrhagic Telanglectasia Scientific Conference, May 20-24, Kemer, Antalya, Turkey. 3(2s): 29 (2011) (abstract only).
Kapur et al., "Abstract 1: Opposing roles for endoglin and soluble endoglin in cardiac remodeling and heart failure," Presented at AHA BCVS Meeting Jul. 20, 2011. Abstract Published in Circulation Research. 109: A1 (2011).

* cited by examiner

*Primary Examiner* — Christine J Saoud
*Assistant Examiner* — Jon M Lockard
(74) *Attorney, Agent, or Firm* — Clark & Elbing LLP

(57) ABSTRACT

Endoglin has now been shown to be an important target of therapy to reduce disease symptoms associated with heart failure, particularly cardiac fibrosis. Soluble Endoglin is identified as an anatogonist to TGFβ1 activity, while membrane-bound Endoglin is identified as a necessary component to promote TGFβ1 activity in heart failure. The present invention therefore features methods and kits for treatment of subject having heart failure or a related disorder by administering a composition that decreases TGFβ1 signaling through either direct inhibition of membrane-bound Endoglin or promoting expression of soluble Endoglin.

22 Claims, 15 Drawing Sheets

Endoglin isoform 1 precursor

```
  1 mdrgtlplav alllascsls ptslaetvhc dlqpvgperg evtyttsqvs kgcvaqapna
 61 ilevhvlfle fptgpsqlel tlqaskqngt wprevllvls vnssvflhlq algiplhlay
121 nsslvtfqep pgvnttelps fpktqilewa aergpitsaa elndpqsill rlgqaqgsls
181 fcmleasqdm grtlewrprt palvrgchle gvaghkeahi lrvlpghsag prtvtvkvel
241 scapgdldav lilqgppyvs wlidanhnmq iwttgeysfk ifpeknirgf klpdtpqgll
301 gearmlnasi vasfvelpla sivslhassc ggrlqtspap iqttppkdtc spellmsliq
361 tkcaddamtl vlkkelvahl kctitgltfw dpsceaedrg dkfvlrsays scgmqvsasm
421 isneavvnil sssspqrkkv hclnmdslsf qlglylsphf lqasntiepg qqsfvqvrvs
481 psvsefllql dschldlgpe ggtveliqgr aakgncvsll spspegdprf sfllhfytvp
541 ipktgtlsct valrpktgsq dqevhrtvfm rlniispdls gctskglvlp avlgitfgaf
601 ligalltaal wyiyshtrsp skrepvvava apassessst nhsigstqst pcstssma
```

Endoglin isoform 2 precursor

```
  1 mdrgtlplav alllascsls ptslaetvhc dlqpvgperg evtyttsqvs kgcvaqapna
 61 ilevhvlfle fptgpsqlel tlqaskqngt wprevllvls vnssvflhlq algiplhlay
121 nsslvtfqep pgvnttelps fpktqilewa aergpitsaa elndpqsill rlgqaqgsls
181 fcmleasqdm grtlewrprt palvrgchle gvaghkeahi lrvlpghsag prtvtvkvel
241 scapgdldav lilqgppyvs wlidanhnmq iwttgeysfk ifpeknirgf klpdtpqgll
301 gearmlnasi vasfvelpla sivslhassc ggrlqtspap iqttppkdtc spellmsliq
361 tkcaddamtl vlkkelvahl kctitgltfw dpsceaedrg dkfvlrsays scgmqvsasm
421 isneavvnil sssspqrkkv hclnmdslsf qlglylsphf lqasntiepg qqsfvqvrvs
481 psvsefllql dschldlgpe ggtveliqgr aakgncvsll spspegdprf sfllhfytvp
541 ipktgtlsct valrpktgsq dqevhrtvfm rlniispdls gctskglvlp avlgitfgaf
601 ligalltaal wyiyshtrey prppq
```

Figure 10

TREATMENT OF HEART FAILURE AND RELATED CONDITIONS

CROSS-REFERENCE TO RELATED APPLICATIONS

This application is the U.S. National Stage of International Application No. PCT/US2012/049018, filed Jul. 31, 2012, which claims benefit of U.S. Provisional Application No. 61/513,930, filed Aug. 1, 2011 and U.S. Provisional Application No. 61/578,477, filed Dec. 21, 2011, the disclosures of which are hereby incorporated by reference in their entirety.

STATEMENT AS TO FEDERALLY FUNDED RESEARCH

This invention was made with United States Government support under grant number HL094909 awarded by the National Institutes for Health. The Government has certain rights to this invention.

BACKGROUND OF THE INVENTION

The invention relates to treatment of heart failure and methods for reducing fibrosis, particularly cardiac fibrosis.

Heart failure is a major cause of morbidity and mortality that affects over 24 million individuals worldwide (Rosamond et al., *Circulation* 117:e25-146, 2008, Cowie et al., *Eur. Heart. J.* 18:208-25, 1997, Davies et al., *Lancet* 358: 439-44, 2001). Irrespective of the injurious mechanism, a decline in left ventricular (LV) function leads to increased LV volume and pressure overload. This hemodynamic stimulus activates several signaling cascades, which alter cardiac structure and function, a process known as cardiac remodeling. Persistent hemodynamic overload leads to cardiomyocyte hypertrophy and interstitial fibrosis, followed by myocyte necrosis and worsening replacement fibrosis. At each phase of cardiac remodeling from acute load to compensatory hypertrophy, various signaling cascades are implicated (Berk et al., *J. Clin. Invest.* 117:568-75, 2007).

SUMMARY OF THE INVENTION

As described in detail below, the inventors have discovered that TGFβ1-mediated signaling through the Endoglin receptor promotes damage to cardiac tissue, particularly cardiac fibrosis, that is observed in individuals suffering from heart failure. Importantly, the inventors have also discovered that the soluble form of Endoglin (sEng) is protective against these effects, presumably by its ability to bind TGFβ1 and thus decrease signaling through the membrane-bound receptor form of Endoglin (mEng). Furthermore, the investigators have identified that reducing expression or activity of mEng also limits TGFβ1 signaling in the heart, resulting in limited fibrosis and improved survival.

Accordingly in a first aspect, the invention features a method for treating or prophylactically treating heart failure (e.g., congestive heart failure, systolic heart failure, or diastolic heart failure), left ventricle dysfunction (e.g., asymptomatic left ventricular dysfunction or left ventricular dysfunction following myocardial infarction), right ventricle dysfunction, hypertension (e.g., adult or pediatric), acute myocardial infarction, or post myocardial infarction in a subject in need thereof. The methods include administering to the subject a therapeutically effective amount of a composition that inhibits Endoglin activity and thereby limits TGFβ1 signaling. The composition may include a soluble polypeptide, where the polypeptide includes the amino acid sequence of soluble Endoglin, e.g., amino acids 26 to 586 of SEQ ID NO:1 or SEQ ID NO:2, or a TGFβ1-inhibitory fragment or analog thereof. In certain embodiments, the soluble Endoglin analog has an amino acid sequence substantially (e.g., at least 70%, 80%, 85%, 90%, 95%, 96%, 97%, 98%, or 99%) identical to amino acids 26 to 586 of SEQ ID NO:1 or SEQ ID NO:2. In other embodiments, the composition includes an antibody, or an antigen-binding fragment thereof (e.g., any antibody or antibody fragment described herein such as a single chain antibody (scFv), Fab, Fab'2, scFv, SMIP, diabody, nanobody, aptamer, or domain antibody). The antibody may be an antagonist of any component of the Endoglin receptor, e.g., that binds mEng. In other embodiments, the composition includes an siRNA molecule that is capable of reducing mEng expression. In particular embodiments, administration of the composition results in a reduction of cardiac fibrosis.

In certain embodiments, the subject is or has suffered from coronary artery disease, congenital heart disease, a heart attack, heart valve disease, or an arrhythmia. In particular embodiments, administration is intravenous, oral, intramuscular, intraarticular, subcutaneous, intraperitoneal, or intralesional.

In another aspect, the invention features a kit including (a) a composition that inhibits Endoglin activity (e.g., any composition described herein or the first aspect of the invention, such as soluble Endoglin, or a fragment or analog thereof); and (b) instructions for administration of the composition for treatment of heart failure, left ventricle dysfunction, right ventricle dysfunction, hypertension, acute myocardial infarction, post myocardial infarction or any other condition or disease described herein.

In another aspect, the invention features a method for reducing fibrosis (e.g., cardiac fibrosis) in a subject. The method includes administering (e.g., intravenously, orally, intramuscularly, intraarticularly, subcutaneously, intraperitoneally, or intralesionally) to the subject an effective amount of a composition that inhibits TGFβ1-mediated Endoglin signaling. The composition may include a soluble polypeptide, where the polypeptide includes the amino acid sequence of soluble Endoglin or a TGFβ1-inhibitory fragment or analog thereof, for example, where the soluble Endoglin includes amino acids 26 to 586 of SEQ ID NO:1 or SEQ ID NO:2 or where the soluble Endoglin analog has an amino acid sequence at least 90% identical to the naturally occurring human soluble Endoglin sequence. In another embodiment, the composition includes an antibody, or an antigen-binding fragment thereof (e.g., where the antibody is an antagonist of the Endoglin receptor, such as an antibody that binds the Endoglin receptor). In other embodiments, the composition includes an siRNA molecule that is capable of reducing Endoglin expression. The subject may be suffering from a condition selected from the group consisting of heart failure (e.g., congestive, systolic, or diastolic heart failure), left ventricle dysfunction (e.g., asymptomatic left ventricular dysfunction or left ventricular dysfunction following myocardial infarction), right ventricle dysfunction, hypertension (e.g., adult hypertension or pediatric hypertension), acute myocardial infarction, or post myocardial infarction. In particular embodiments, the subject is suffering or has suffered from coronary artery disease, congenital heart disease, a heart attack, heart valve disease, or an arrhythmia.

By "subject" is meant a human or non-human animal (e.g., a mammal).

By "treating" a disease, disorder, or condition in a subject is meant reducing at least one symptom of the disease, disorder, or condition by administrating a therapeutic agent to the subject.

By "treating prophylactically" a disease, disorder, or condition in a subject is meant reducing the frequency of occurrence of or reducing the severity of a disease, disorder or condition by administering a therapeutic agent to the subject prior to the onset of disease symptoms.

By "soluble Endoglin" is meant a polypeptide that includes the extracellular domain of Endoglin, but does not include the transmembrane or cytoplasmic domains of Endoglin and has the ability to decrease TGFβ1-mediated activation of the Endoglin receptor. Soluble Endoglin can include amino acids 26 to 586 of SEQ ID NO:1 or SEQ ID NO:2 shown in FIG. 10.

By "soluble Endoglin fragment" is meant a fragment of at least 4, 5, 6, 8, 10, 15, 20, 25, 30, 40, 50, 60, 70, 80, 100, 125, 150, 175, 200, 225, 250, 300, 350, 400, or 450 amino acids of soluble Endoglin.

By "membrane-bound Endoglin (mEng)" is meant the full-length Endoglin including the extracellular, trans-membrane, and cytoplasmic domains (amino acids 1-633). Both the long (L)- and short (S)-isoforms of Endoglin are included in the definition of mEng.

By "substantial identity" or "substantially identical" is meant a polypeptide or polynucleotide sequence that has the same polypeptide or polynucleotide sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

Other features and advantages of the invention will be apparent from the following Detailed Description, the drawings, and the claims.

BRIEF DESCRIPTION OF THE DRAWINGS

FIG. 1A is a representative western blot of Endoglin expression in isolated mouse endothelium, cardiomyocytes, and cardiac fibroblasts. FIG. 1B is a western blot showing reduced Endoglin expression in total left ventricular lysates from $Eng^{+/-}$ mice as compared to WT (n=3/group). FIGS. 1C and 1D are graphs showing that left ventricular Endoglin mRNA and protein expression are increased in WT mice after thoracic aortic constriction (TAC). $Eng^{+/-}$ mice exhibit reduced Endoglin mRNA and protein levels compared to WT mice (n=6/group). FIG. 1E is a graph showing that circulating levels of soluble Endoglin are increased after two weeks, then reduced to normal in WT mice after TAC. Levels of sEng are significantly lower in $Eng^{+/-}$ mice compared to WT across all time points of TAC (n=6/group). FIG. 1F is an M-mode echocardiogram showing progressive LV dilatation in WT mice compared to preserved LV function in $Eng^{+/-}$ mice after TAC. FIG. 1G is a graph showing representative left ventricular pressure-volume loops after four weeks of TAC, which show less volume overload and higher LV systolic pressure in $Eng^{+/-}$ mice compared to WT mice after TAC. FIG. 1H is a graph showing Kaplan-Meier survival curves showing markedly improved survival in $Eng^{+/-}$ mice compared to WT mice after ten weeks of TAC (n=8/group). (*, $p<0.05$ vs. WT Sham; †, $p<0.05$ vs. Eng+/−Sham; ‡, $p<0.05$ vs. WT at the corresponding time point.)

FIG. 3A is a photomicrograph showing representative histologic staining and FIG. 3B is a bar graph of left ventricular cardiomyocyte cross-sectional area showing hypertrophy in both WT and $Eng^{+/-}$ mice after four weeks of TAC. FIGS. 3C and 3D are graphs showing LV expression of fetal genes associated with cardiac hypertrophy (β-MHC and SERCa) show similar patterns in WT and $Eng^{+/-}$ mice after four weeks of TAC. FIG. 3E is a graph showing LV protein expression of calcineurin in WT and $Eng^{-/-}$ mice after four weeks of TAC. FIG. 3F is a photomicrograph showing representative histologic staining of LV myocardial capillaries using an anti-CD31 antibody demonstrating increased capillary density in $Eng^{+/-}$ mice, as compared to WT mice, after four weeks of TAC. FIGS. 3G and 3H are bar graphs showing quantitation of myocardial capillarity in the LV after four weeks of TAC in WT and $Eng^{+/-}$ mice.

FIG. 5A is a photomicrograph of representative histologic staining of left ventricular collagen abundance in WT and $Eng^{+/-}$ mice after TAC. FIG. 5B is a graph showing quantitation of percent LV fibrosis showing significantly less fibrosis in $Eng^{+/-}$ mice compared to WT after TAC (n=6/group). FIG. 5C is a graph showing that levels of LV Type I Collagen mRNA are reduced in Eng+/− mice after four weeks of TAC, as compared to WT (n=6/group). FIG. 5D is a graph showing that LV Type I Collagen protein expression increases in a time-dependent manner in WT mice after TAC. Significantly lower levels in $Eng^{+/-}$ mice were observed at each time point (n=6/group). FIG. 5E is a graph showing increased levels of TGFβ1 mRNA in both WT and $Eng^{+/-}$ mice after four weeks of TAC. FIG. 5F is a graph and western blot image showing increased pSmad-2/3 expression in WT mice after TAC. There was no change in pSmad-2/3 expression in $Eng^{+/-}$ mice after TAC.

FIG. 6A shows type I collagen mRNA expression after ten weeks of TAC in WT and $Eng^{+/-}$ mice. FIG. 6B is a graph showing levels of active TGFβ1 protein expression in LV tissue lysates after four weeks of TAC. FIG. 6C shows that mRNA expression of the downstream target of TGFβ1 activity, PAI-1, is significantly attenuated in Eng$^{+/-}$ mice subjected to TAC as compared to WT controls. FIG. 6D shows that protein expression of pSmad-1/5/8 expression is unchanged in WT mice, but increased in Eng$^{+/-}$ mice after four weeks of TAC (quantitation in bar graph for n=6 mice/group under representative western blot).

FIG. 7A shows that treatment with an anti-Endoglin antibody reduced type I collagen mRNA (bar graph) and protein expression (western blot) in hCF. FIG. 7B shows that silencing Endoglin expression attenuated TGFβ1 induced type I collagen mRNA (bar graph) and protein expression (western blot) in hCF. FIG. 7C is an image of a western blot showing that adenoviral mediated overexpression of full-length Endoglin (Ad-FL-Eng) attenuates TGFβ1-induced type I collagen protein synthesis in hCF. FIG. 7D shows levels of soluble Endoglin in conditioned media from hCF transfected with Ad-FL-Eng. FIG. 7E shows that recombinant human soluble Endoglin (RhsEng) attenuates TGFβ1-induced type I collagen protein expression in a dose-dependent manner (quantitation of western blot shown in bar graph). FIG. 7F shows that conditioned media from COS-7 cells transfected with an adenovirus over-expressing human sEng (AdhsEng) attenuated TGFβ1 induced type I collagen protein synthesis (bar graph and western blot) and pSmad-2/3 expression (western blot) in a dose-dependent manner.

FIGS. 8A-8B show that silencing Endoglin expression attenuates TGFβ1-induced PAI-1 and CTGF mRNA expression in human cardiac fibroblasts. FIG. 8C shows that recombinant human soluble Endoglin (RhsEng) attenuates TGFβ1-induced Type I collagen mRNA expression in a dose dependent manner in hCF. FIG. 8D shows that COS-7 cells transfected with AdhsEng demonstrate a dose-dependent increase in levels of sEng detected in the culture media.

FIG. 9A is a graph showing that intravenous injections of AdhsEng increased circulating levels of human soluble Endoglin in WT mice without affecting levels of mouse sEng. FIG. 9B is a representative histologic image showing reduced picrosirius red staining for collagen in WT mice treated with AdhsEng compared to mice treated with a null adenovirus (AdNull). FIG. 9C is a graph showing that levels of LV type I collagen mRNA were significantly reduced in WT mice treated with AdhsEng as compared to AdNull controls. FIG. 9D is a schematic diagram demonstrating that reduced mEng expression in Eng$^{+/-}$ mice attenuates TGFβ1 induced pSmad-2/3 and type I collagen expression, thereby limiting cardiac fibrosis. Treatment with sEng replicates the Endoglin-deficient condition by reducing pSmad-2/3 and type I collagen expression. Soluble Endoglin may therefore serve as a ligand trap for TGFβ1.

FIG. 10 is the amino acid sequences of Endoglin isoform 1 precursor and the Endoglin isoform 2 precursor.

DETAILED DESCRIPTION

Figures 1A, 1B, 1C, 1D, 1E:
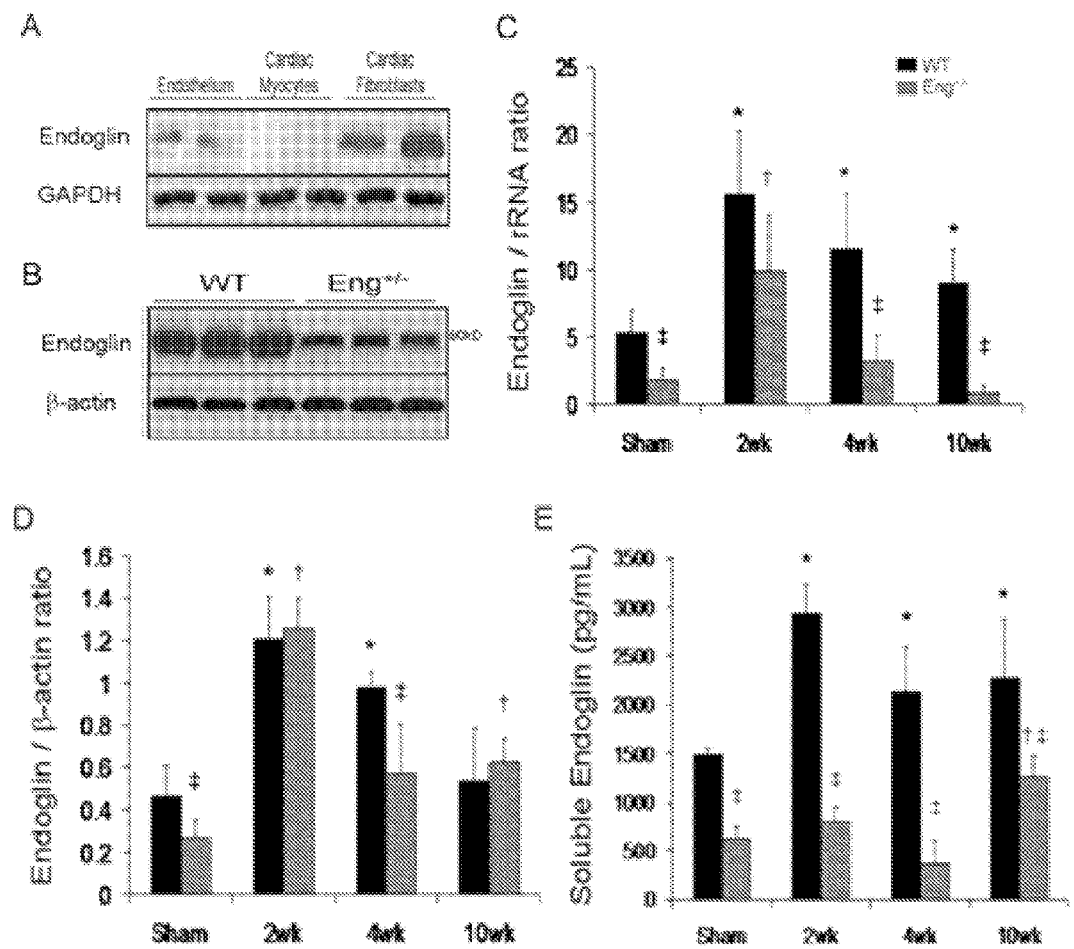
FIGS. 1A-1H are graphs and images showing that reduced Endoglin expression correlates with improved cardiac function and survival in pressure overload-induced heart failure.
Figure 1F:
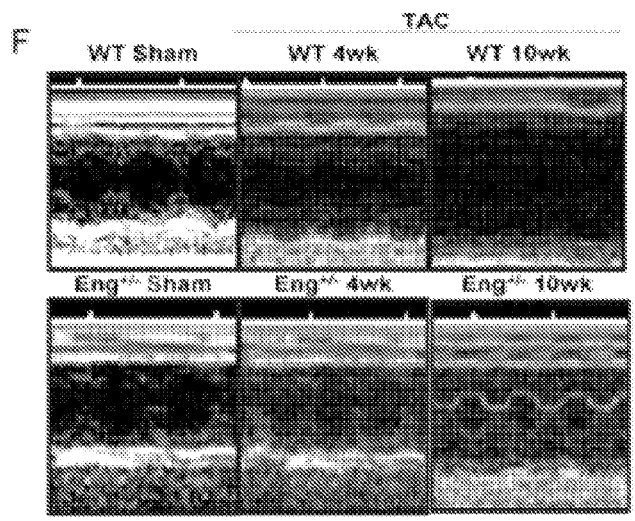
Figure 1G:
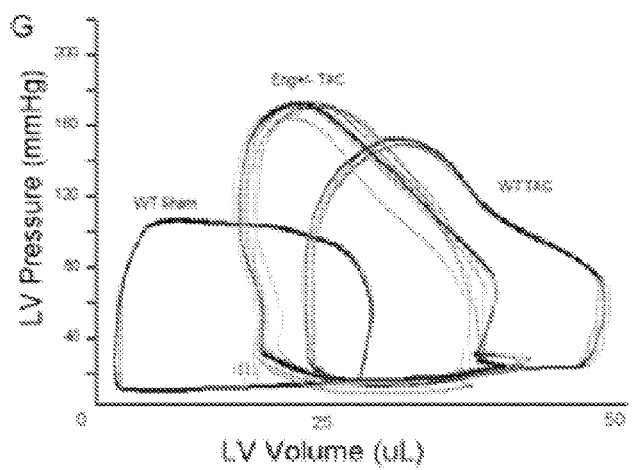
Figure 1H:
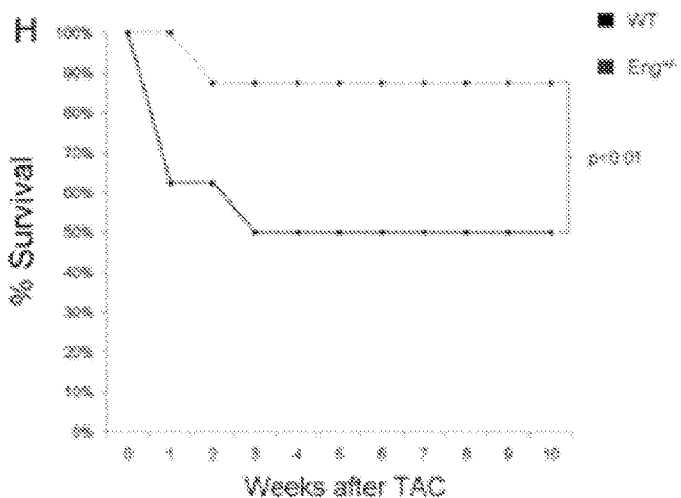

We have discovered that soluble Endoglin acts as a negative regulator of TGFβ1-signaling through the Endoglin receptor and that inhibition using soluble Endoglin (sEng) results in a reduction in the pathophysiology associated with heart failure, particularly cardiac fibrosis. Based on this discovery, the present invention features methods for treating heart failure by administering a composition that inhibits TGFβ1 signaling through the Endoglin receptor pathway, such as soluble Endoglin.

Endoglin

Endoglin (Eng; CD105) is a 180 kDa membrane-associated dimeric glycoprotein (mEng) that is also found as a circulating form composed of the extracellular domain, known as soluble Endoglin (sEng). Endoglin plays an important role in vascular remodeling. Under basal conditions the vascular endothelium responds to TGFβ1 through the TGF-β type II receptor in association with either of two type I signaling receptors known as activin like kinase (ALK)1 and ALK5, which promote either a proliferative or quiescent phenotype respectively. Endoglin modulates responses to TGF-β1 and is implicated in the regulation of the switch from ALK5 to ALK1 signaling pathways.

The role of Endoglin as a modulator of TGF-β1 signaling in cardiac fibroblasts and heart failure, where fibrosis plays a major role, prior to the present invention, had not been explored. While several lines of evidence suggest that Endoglin plays a critical role in maintaining vascular homeostasis (Lopez-Novoa et al., Am. J. Physiol. Heart Circ. Physiol. 299:H959-74, 2010), the role of Endoglin in cardiac remodeling and heart failure had remained largely ignored.

TGFβ1, Endoglin, and Heart Failure

TGFβ1 is a powerful cytokine positioned centrally among critical processes known to modulate cardiomyocyte hypertrophy and fibrosis. As described below, Endoglin plays an important role in the pathophysiology of cardiac remodeling in pressure overload-induced heart failure. By first identifying that cardiac expression of Endoglin, a critical regulatory protein for TGFβ1 signaling, is primarily restricted to non-cardiomyocyte cell populations, we were able study the effects of reduced TGFβ1 signaling in cardiac fibroblasts in vivo. Similar to our observations in human subjects with heart failure, we observed increased mEng and sEng expression in a mouse model of pressure overload-induced heart failure. Importantly, when compared to WT controls, the pattern of mEng and sEng expression were similar in Eng$^{+/-}$ mice subjected to TAC; however, the expression levels were significantly lower. Reduced mEng expression correlated with a pro-survival cardiac phenotype in heart failure and was associated with preserved cardiomyocyte hypertrophy, a modest increase in myocardial capillarity, and significantly reduced cardiac fibrosis. We then demonstrated the dependence of TGFβ1 signaling on mEng expression in human cardiac fibroblasts using loss-of-function studies. Paradoxically, mEng over-expression similarly attenuated TGFβ1 induced Type I collagen synthesis and implicated sEng as an autocrine inhibitor of TGFβ1 activity in hCF. Treatment with sEng as either a recombinant peptide or by adenoviral over-expression in vitro mirrored the Endoglin-deficient condition by limiting TGFβ1 signaling and type I collagen synthesis. Finally, we began to explore the potential clinical utility of sEng in pressure overload-induced heart failure and observed reduced cardiac fibrosis in mice treated with an adenovirus over-expressing human sEng. Together, these findings identify Endoglin as an important participant in the biology of cardiac fibrosis (FIG. 5D) and remodeling and as a potentially novel therapeutic target to improve survival in heart failure.

The pro-survival phenotype we observed in Eng$^{+/-}$ mice is similar to previously described models of physiologic hypertrophy whereby cardiomyocyte hypertrophy is supported by a parallel increase in myocardial capillarity. In our model, the most profound observation was a nearly complete loss of cardiac fibrosis without affecting cardiac hypertrophy. Improved survival has also been observed in pre-clinical and clinical studies of anti-fibrotic therapy in heart failure (Zannad et al., *Circulation* 102:2700-6, 2000; Kuwahara et al., *Circulation* 106:130-5, 2002). In our model, we not only observed improved survival, but also preserved cardiac function and no cardiac dilatation despite chronic LV pressure overload. These findings highlight the important contribution of cardiac fibrosis to adverse cardiac remodeling and in the pathogenesis of end-stage dilated cardiomyopathy.

Figures 5A, 5B, 5C, 5D, 5E, 5F:
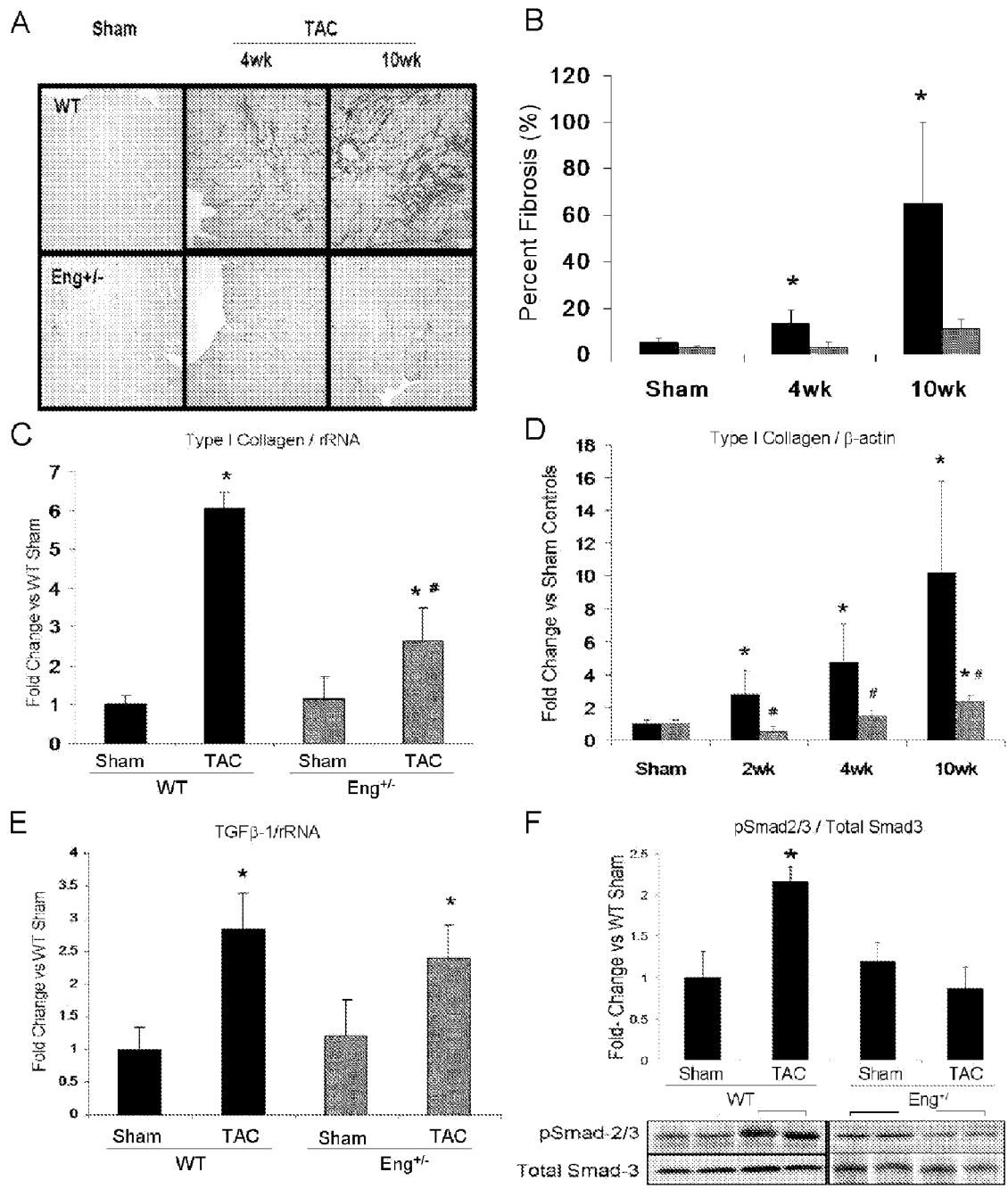
FIGS. 5A-5F are images and graphs showing reduced cardiac fibrosis in $Eng^{+/-}$ mice after pressure overload-induced heart failure.

Soluble Endoglin is believed to result from proteolytic cleavage of the Endoglin extracellular domain by matrix metalloproteinase 14 (MT1-MMP). Once released, overexpression of the Endoglin extracellular domain negatively regulates TGFβ1 activity (Venkatesha et al., *Nat. Med.* 12:642-9, 2006, Letamendia et al., *J. Biol. Chem.* 273: 33011-9, 1998), where sEng may serve as a ligand trap for TGFβ1 (Venkatesha et al., *Nat. Med.* 12:642-9, 2006) (FIG. 5D). Our data show that sEng is an important negative regulator of TGFβ1 activity in human cardiac fibroblasts, as evidenced by reduced pSmad-2/3 and type 1 collagen expression. Shedding of sEng in heart failure may thus serve as a protective mechanism to reduce stimulation of cardiac fibrosis by TGFβ1.

sEng may also bind to pro-angiogenic TGFβ-family members such as BMP9 and thereby negatively regulate tissue angiogenesis (Castonguay et al., *J. Biol. Chem.* 286: 30034-46, 2011), which is consistent with our observations, as we noted increased myocardial capillary density in Eng$^{+/-}$ mice, who manifested significantly lower levels of sEng throughout all phases of cardiac pressure overload, despite variable expression of mEng at each time point.

Furthermore, we observed increased pSmad-1/5/8 expression in Eng$^{+/-}$ mice subjected to TAC as compared to WT controls, suggesting that other TGFβ-family ligands may be more active in Eng$^{+/-}$ mice. Thus, reduced mEng expression may promote survival by limiting cardiac fibrosis in vivo, while reduced sEng expression promotes myocardial capillarity by limiting ligand-trapping of pro-angiogenic cytokines such as BMP9. Finally, over-expressing sEng may limit cardiac fibrosis and adverse remodeling in heart failure by replicating the Endoglin-deficient condition. Together, our data highlight that the balance between mEng versus sEng expression is important in regulating cardiac remodeling in pressure overload-induced heart failure.

Another important finding is that Endoglin plays in promoting pSmad-2/3 phosphorylation and subsequent cardiac fibrosis (FIG. 5F). Several prior reports have demonstrated that Smad-2/3 promotes cardiac fibrosis and adverse remodeling (Letamendia et al., *J. Biol. Chem.* 273:33011-9, 1998; Dobaczewski et al., *Circ. Res.* 107:418-28, 2010). In support of our observations, mice with conditional knockdown of the Type II TGFβ-receptor (TBR2$^{CKD}$) subjected to TAC demonstrate reduced cardiac interstitial fibrosis, enhanced myocardial capillarity, and preserved cardiac function (Huang et al., *Hypertension* 55:1165-71, 2010). Compared to controls, levels of pSmad3 were also reduced in TBR2$^{CKD}$ mice after TAC. Because Endoglin requires TBRII for effective TGFβ1-ligand binding (Barbara et al., *J. Biol. Chem.* 274:584-94, 1999), our model closely replicates the phenotype of the TBR2$^{CKD}$ mice after TAC and we observe a similar loss of pSmad-2/3 expression in Eng$^{+/-}$ mice. Furthermore, mice lacking expression of bone morphogenetic protein Type 2 receptor (BMPR2$^{-/-}$) have been studied as models of pulmonary hypertension. In these mice, reduced pSmad-1/5/8 expression is associated with right ventricular (RV) failure in the presence of chronic RV pressure overload (Koitabashi et al., *J. Clin. Invest.* 121: 2301-12, 2011; Upton et al., *J. Biol. Chem.* 284:15794-804, 2009). Ligands for BMPR-2, such as BMP7 have also demonstrated a potent anti-fibrotic effect in mouse models of heart failure (Long et al., *Circulation* 119:566-76, 2009), further supporting the concept that promoting pSmad-1/5/8 activity may have beneficial effects on cardiac function. Taken together, the findings associated with the TBRII$^{CKD}$ and BMPR2$^{-/-}$ mouse models highlight the beneficial effects of reduced Smad-2/3 and enhanced Smad-1/5/8 signaling. Importantly, Endoglin may bind ligands associated with both TBRII and BMPR2, such as TGFβ1 and BMPs-2, -4, -7, and -9 (Zeisberg et al., *Nat. Med.* 13:952-61, 2007), thus positioning this auxiliary receptor in a critical location between these important Type II receptors that signal through Smad-2/3 and Smad-1/5/8 respectively.

In conclusion, Endoglin regulates cardiac remodeling in response to LV pressure overload. Our results highlight the opposing roles of mEng and sEng as modulators of TGFβ1 activity in cardiac fibroblasts. Furthermore, the redundancy of ligands, receptors, and downstream Smad-effector proteins further supports the importance of our observation that Endoglin plays an important role in mediating TGFβ1 signaling via pSmad-2/3. Thus, therapies targeting Endoglin biology in heart failure may improve clinical outcomes in individuals affected by this devastating condition.

Treatment of a Subject Suffering from Heart Failure or a Related Disease

The methods of the present invention may be used to treat subjects suffering from heart failure or a related condition, particularly those that are associated with or caused by cardiac fibrosis.

Heart failure occurs when the heart can no longer pump enough blood to the rest of the body. Heart failure is most commonly caused by coronary artery disease but can result from other causes as well, including cardiomyopathy (weakening of heart muscle by infection), congenital heart disease, heart attack, heart valve disease, and certain arrhythmias. Other diseases that can contribute to heart failure include emphysema, overactive thyroid, severe anemia, and underactive thyroid. The methods described herein may involve treatment or prophylactic treatment of a subject that is suffering from any of these conditions or diseases.

Symptoms of heart failure include cough, fatigue, weakness, faintness, loss of appetite, need to urinate at night, fast or irregular pulse or heart palpitations, shortness of breath following activity or after lying down, swollen liver or abdomen, swollen feet, ankles, or legs, waking up from sleep after a couple of hours due to shortness of breath, weight gain, distended neck veins, and fluid buildup in lungs. The method described herein may treat any one or more of these symptoms.

Other diseases that may be treated using the methods described herein include left ventricle dysfunction (e.g., asymptomatic or following myocardial infarction), hypertension (e.g., adult or pediatric), acute myocardial infarction, and post myocardial infarction.

Soluble Endoglin

The methods of the invention can, in certain embodiments, employ soluble Endoglin, a soluble Endoglin fragment, or a soluble Endoglin analog, e.g., a fragment or an analog that retains the ability to bind TGFβ1.

Full length Endoglin is a 180 kDa homodimeric co-receptor for members of the TGF-β superfamily. Two isoforms of Endoglin are known: a 633 amino acid protein and 600 amino acid protein. These two forms differ in the length of their cytoplasmic tail; the longer form has 47 amino acid tail (L-mEng), whereas the shorter form has a 14 amino acid cytoplasmic tail (S-mEng). The amino acid sequences of Endoglin are described in NCBI accession numbers NP_001108225 and NP_000109.1 and are shown in FIG. 10. The mature endoglin sequences include amino acids 26 to 658 of isoform 1 and amino acids 26-625 of isoform 2. In both isoforms, amino acids 587 to 611 are predicted to be the transmembrane domain. The corresponding extracellular region (amino acids 26 to 586 or 27 to 586) of Endoglin, fragments thereof, or analogs thereof may therefore be used in the invention.

The methods described herein can also use a fragment of soluble Endoglin (e.g., any of those described herein. Preferred fragments are capable of binding TGFβ1, e.g., with at least 1%, 5%, 10%, 15%, 20%, 25%, 35%, 50%, 75%, 80%, 85%, 90%, 95%, 97%, or 99% of the binding affinity of soluble Endoglin or the naturally occurring form of soluble Endoglin.

The methods described herein can also use a soluble Endoglin analog. In certain embodiments, the analog has at least 60%, 70%, 80%, 85%, 90%, 95%, 96%, 97%, 98%, or 99% sequence identity to soluble Endoglin or to a soluble Endoglin fragment. Preferred analogs are capable of binding TGFβ1, e.g., with at least 1%, 5%, 10%, 15%, 20%, 25%, 35%, 50%, 75%, 80%, 85%, 90%, 95%, 97%, or 99% of the binding affinity of soluble Endoglin.

Antibodies

The methods of the invention can employ an antibody that prevents Endoglin activity by TGFβ1 or an antigen-binding fragment thereof. In certain embodiments, the antibody specifically binds to mEng or to sEng. The antibody can bind specifically to the extracellular domain (ECD) of mEng, the residual membrane-associated component of mEng after cleavage of the ECD, or to circulating sEng. The antibody can be a monoclonal or a polyclonal antibody. In certain embodiments, the antibody is humanized. The antibody or antibody fragment can be a single chain antibody (scFv), Fab, Fab'2, scFv, SMIP, diabody, nanobody, aptamer, or domain antibody.

Antibodies (e.g., monoclonal, polyclonal, poly-specific, or mono-specific antibodies) against Endoglin (e.g., antagonistic antibodies) can be made using any of the numerous methods for making antibodies known in the art. In one example, the relevant Endoglin sequence is produced as a C-terminal fusion with glutathione S-transferase (GST) (Smith et al., *Gene* 67:31-40, 1988). The fusion protein is purified on glutathione-Sepharose beads, eluted with glutathione, cleaved with thrombin (at an engineered cleavage site), and purified for immunization of rabbits. Primary immunizations are carried out with Freund's complete adjuvant and subsequent immunizations with Freund's incomplete adjuvant. Antibody titers are monitored by Western blot and immunoprecipitation analyses using the thrombin-cleaved protein fragment of the GST fusion protein. Immune sera are affinity purified using CNBr-Sepharose-coupled protein. Antiserum specificity can be determined using a panel of unrelated GST proteins.

Alternatively, monoclonal antibodies that specifically bind Endoglin can be prepared using standard hybridoma technology (see, e.g., Kohler et al., *Nature* 256:495-7, 1975; Kohler et al., *Eur. J. Immunol.* 6:511-9, 1976; Kohler et al., *Eur. J. Immunol.* 6:292-5, 1976; Hammerling et al., *Monoclonal Antibodies and T Cell Hybridomas*, Elsevier, N.Y., 1981). Once produced, monoclonal antibodies can also be tested for specific recognition by Western blot or immuno-precipitation analysis. Alternatively, monoclonal antibodies can be prepared using the polypeptide of the invention described above and a phage display library (Vaughan et al., *Nat. Biotechnol.* 14:309-14, 1996).

In order to generate polyclonal antibodies on a large scale and at a low cost an appropriate animal species can be chosen. Polyclonal antibodies can be isolated from the milk or colostrum of, e.g., immunized cows. Bovine colostrum contains 28 g of IgG per liter, while bovine milk contains 1.5 g of IgG per liter (Ontsouka et al., *J. Dairy Sci.* 86:2005-11, 2003). Polyclonal antibodies can also be isolated from the yolk of eggs from immunized chickens (Sarker et al., *J. Pediatr. Gastroenterol. Nutr.* 32: 19-25, 2001).

Useful antibodies can be identified in several different screening assays. First, antibodies are assayed by ELISA to determine whether they are specific for the immunizing antigen (i.e., Endoglin). Using standard techniques, ELISA plates are coated with immunogen, the antibody is added to the plate, washed, and the presence of bound antibody detected by using a second antibody specific for the Ig of the species in which the antibody was generated.

RNA Interference

The methods described herein can also use RNAi to inhibit Endoglin expression. RNA interference (RNAi) is a mechanism of post-transcriptional gene silencing (PTGS) in which double-stranded RNA (dsRNA) corresponding to a gene or mRNA of interest is introduced into an organism, resulting in the degradation of the corresponding mRNA. In the RNAi reaction, both the sense and anti-sense strands of a dsRNA molecule are processed into small RNA fragments or segments ranging in length from 21 to 23 nucleotides (nt) and having 2-nucleotide 3' tails. Alternatively, synthetic dsRNAs, which are 21 to 23 nt in length and have 2-nucleotide 3' tails, can be synthesized, purified, and used in the reaction. These 21 to 23 nt dsRNAs are known as "guide RNAs" or "short interfering RNAs" (siRNAs).

The siRNA duplexes then bind to a nuclease complex composed of proteins that target and destroy endogenous mRNAs having homology to the siRNA within the complex. The complex functions by targeting the homologous mRNA molecule through base pairing interactions between one of the siRNA strands and the endogenous mRNA. The mRNA is then cleaved approximately 12 nt from the 3' terminus of the siRNA and degraded. In this manner, specific genes can be targeted and degraded, thereby resulting in a loss of protein expression from the targeted gene. siRNAs can also be chemically synthesized or obtained from a company that chemically synthesizes siRNAs (e.g., Dharmacon Research Inc., Pharmacia, or ABI).

Endoglin RNAi molecules are commercially available and can be obtained from a variety of sources, including Santa Cruz Biotechnology (siRNA; Cat. No. sc-35302).

The specific requirements and modifications of dsRNA are described in PCT Publication No. WO 01/75164, and in U.S. Patent Application Publication No. 20060067937 and PCT Publication No. WO 06/034507, incorporated herein by reference.

Administration and Dosage

The methods described herein feature administration of a composition that inhibits TGFβ1-mediated Endoglin signaling. The composition can be formulated for use in a variety of drug delivery systems. One or more physiologically acceptable excipients or carriers can also be included in the composition for proper formulation. Suitable formulations for use in the present invention are found in *Remington's Pharmaceutical Sciences*, Mack Publishing Company, Philadelphia, Pa., 17th ed., 1985. For a brief review of methods for drug delivery, see, e.g., Langer (Science 249: 1527-1533, 1990).

The pharmaceutical composition can be used for parenteral, intranasal, topical, oral, or local administration, such as by a transdermal means, for prophylactic and/or therapeutic treatment. The pharmaceutical composition can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that include the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques or may be sterile filtered. The resulting aqueous solutions may be packaged for use as is or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In prophylactic applications, compositions can be administered to a subject diagnosed as being at risk for heart failure (e.g., having lower levels of soluble Endoglin, as described in U.S. patent application Ser. No. 13/288,493). Compositions of the invention can be administered to the subject (e.g., a human) in an amount sufficient to delay, reduce, or preferably prevent the onset of the disorder. In therapeutic applications, compositions are administered to a subject (e.g., a human) already suffering from heart failure of any of the disorders described herein in an amount sufficient to cure or at least partially arrest the symptoms of the disorder and its complications. An amount adequate to accomplish this purpose is defined as a "therapeutically effective amount," an amount of a compound sufficient to substantially improve at least one symptom associated with the disease or a medical condition. For example, in the treatment of heart failure, an agent or compound that decreases, delays, suppresses, or arrests any symptom of the condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Amounts effective for this use may depend on the severity of the disease or condition and the weight and general state of the subject. The therapeutically effective amount of the compositions of the invention and used in the methods of this invention applied to mammals (e.g., humans) can be determined by the treating physician with consideration of individual differences in age, weight, and the condition of the mammal. The agents of the invention are administered to a subject (e.g. a mammal, such as a human) in an effective amount, which is an amount that produces a desirable result in a treated subject (e.g., reduction of cardiac fibrosis). Therapeutically effective amounts can also be determined empirically by those of skill in the art.

Single or multiple administrations of the compositions of the invention including an effective amount can be carried out with dose levels and pattern being selected by the treating physician. The dose and administration schedule can be determined and adjusted based on the severity of the disease or condition in the subject, which may be monitored throughout the course of treatment according to the methods commonly practiced by clinicians or those described herein.

The compounds of the present invention may be used in combination with either conventional methods of treatment or therapy or may be used separately from conventional methods of treatment or therapy.

When the compounds of this invention are administered in combination therapies with other agents, they may be administered sequentially or concurrently to an individual. Alternatively, pharmaceutical compositions according to the present invention may be comprised of a combination of a compound of the present invention in association with a pharmaceutically acceptable excipient, as described herein, and another therapeutic or prophylactic agent known in the art.

The following examples are intended to illustrate, rather than limit, the invention.

Example 1

Figure 2:
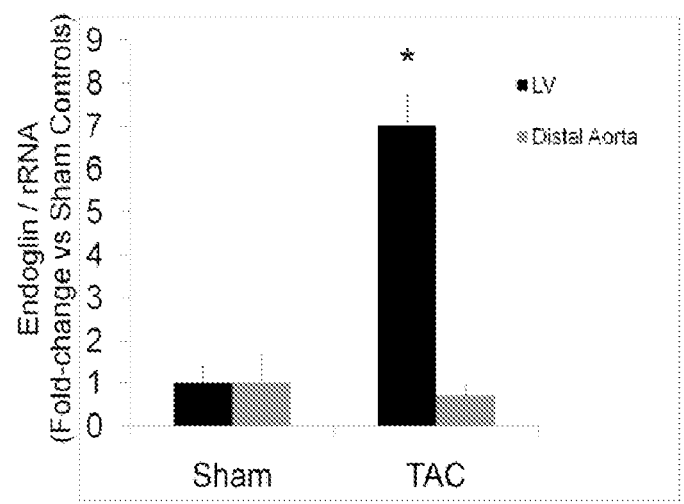
FIG. 2 is a graph showing that increased Endoglin mRNA expression in the LV, but not in the distal aorta, of WT mice that have been subjected to TAC.

Endoglin Expression in Cardiac Fibroblast During Left Ventricle Pressure Overload To explore the role of Endoglin in heart failure, we first demonstrated that Endoglin is primarily expressed by isolated non-cardiomyocyte populations including cardiac fibroblasts and endothelium (FIG. 1A). We then employed the well-established mouse model of LV pressure overload induced by thoracic aortic constriction (TAC), followed by tissue characterization at two, four, and ten weeks of heart failure. Compared to WT mice, baseline Endoglin expression in the LV was significantly lower in $Eng^{+/-}$ mice (FIG. 1B). After TAC, LV mEng mRNA and protein expression were significantly increased by two weeks, then remained elevated up to four weeks after TAC, and returned to near normal by ten weeks in WT mice (FIGS. 1C and 1D). No change in Endoglin expression was observed in the aorta distal to the site of TAC ligature (FIG. 2). Serum levels of sEng were also elevated within two weeks and normalized by four and ten weeks after TAC (FIG. 1E). In Eng$^{+/-}$ mice, overall mEng and sEng expression were significantly reduced compared to WT mice (FIGS. 1C-1E). The Eng$^{+/-}$ mice, however, exhibited a similar pattern of expression as WT mice. LV mEng mRNA and protein expression were increased at two weeks after TAC and reduced to near-normal values by four and ten weeks. Across all time points, sEng levels were lower in Eng$^{+/-}$ mice compared to WT. These findings suggest that pressure overload directly stimulates left ventricular expression of mEng without affecting systemic mEng expression. During the acute phase of pressure overload, sEng levels increase concordantly with LV mEng levels in WT mice, suggesting a possible cardiac origin for this circulating form of Endoglin. Importantly, Eng$^{+/-}$ mice exhibit reduced levels of mEng and sEng expression in response to pressure overload-induced heart failure.

Example 2

Reduced Endoglin Expression Promotes a Pro-Survival Cardiac Phenotype in Heart Failure We next examined the functional impact of reduced Endoglin expression during pressure overload-induced heart failure. Eng$^{+/-}$ mice demonstrated preserved cardiac function by echocardiography and pressure volume loop analysis and improved survival compared to WT mice after TAC (88% versus 50%, respectively, p<0.01) (FIGS. 1I-1J). Consistent with these observations, WT mice manifest significantly reduced total body weight at both four and ten weeks after TAC, while Eng$^{+/-}$ mice did not (Table 1).

TABLE 1

Physiologic findings in WT vs Eng+/− mice after TAC.

|  | Sham | TAC 4 weeks | TAC 10 weeks |
|---|---|---|---|
| Mass | | | |
| Total Body Weight (g) | | | |
| WT | 35 + 3.9 | 29 + 3.1* | 26 + 2.2** |
| Eng$^{+/-}$ | 34 + 1.2 | 34 + 4.6# | 35 + 3.7# |
| LV weight (g)/Tibia length (mm) | | | |
| WT | 0.007 + 0.001 | 0.011 + 0.0001* | 0.015 + 0.002** |
| Eng$^{+/-}$ | 0.005 + 0.0007# | 0.009 + 0.001*# | 0.011 + 0.001# |
| Total Lung weight (g) | | | |
| WT | 0.009 + 0.0007 | 0.24 + 0.01* | 0.023 + 0.005** |
| Eng$^{+/-}$ | 0.008 + 0.0003# | 0.019 + 0.01* | 0.015 + 0.005**# |
| Hemodynamic Data | | | |
| Heart Beat (beats/min) | | | |
| WT | 535 + 45 | 553 + 40 | 573 + 93 |
| Eng$^{+/-}$ | 549 + 32 | 522 + 49 | 547 + 32 |
| LV End-Systolic Pressure (mmHg) | | | |
| WT | 115 + 12 | 130 + 22 | 98 + 42 |
| Eng$^{+/-}$ | 99 + 15 | 157 + 19*# | 167 + 14*# |
| LV End-Diastolic Pressure (mmHg) | | | |
| WT | 11 + 4 | 31 + 7* | 23 + 7* |
| Eng$^{+/-}$ | 9 + 5 | 24 + 12* | 25 + 4* |
| dP/dtmax | | | |
| WT | 9000 + 1263 | 5184 + 1092* | 3959 + 1980* |
| Eng$^{+/-}$ | 8141 + 1183 | 7127 + 2615# | 7015 + 712# |
| dP/dtmin | | | |
| WT | 8288 + 1446 | 5614 + 1195* | 3954 + 1955* |
| Eng$^{+/-}$ | 8015 + 1563 | 7281 + 2204# | 7336 + 907# |
| Echocardiographic Data | | | |
| LV End-Diastolic Diameter (mm) | | | |
| WT | 2.4 + 0.4 | 3.9 + 0.4* | 4.5 + 1.8* |
| Eng$^{+/-}$ | 1.8 + 0.1# | 3.4 + 0.6* | 2.6 + .03*# |
| Fractional Shortening (%) | | | |
| WT | 72 + 9 | 42 + 4* | 18 + 15* |
| Eng$^{+/-}$ | 57 + 8# | 40 + 7 | 67 + 10# |
| Posterior Wall Thickness (mm/) | | | |
| WT | 0.9 + 0.2 | 1.4 + 0.3* | 1.3 + 0.3* |
| Eng$^{+/-}$ | 0.5 + 0.04# | 1.3 + 0.2* | 2.3 + 0.1*# |

*p < 0.05: 4 wk vs Before TAC;
**p < 0.05: 10 wk vs Before TAC;
p < 0.05: Eng+/− vs WT Compared to baseline values, lung weights were significantly increased in both mouse groups across all periods of TAC; however, lung weights were lower in Eng$^{+/-}$ mice at ten weeks after TAC compared to WT (Table 1). At both four and ten weeks after TAC, LV systolic (LVSP) and end-diastolic pressure (LVEDP) were increased in both WT and Eng$^{+/-}$ mice compared to their respective sham operated controls. While LVEDP was not significantly different between WT and Eng$^{+/-}$ mice, LVSP was significantly higher in Eng$^{+/-}$ mice compared to WT at both four and ten weeks after TAC. LV contractility (dP/dt$_{max}$) significantly decreased in a time-dependent manner in WT mice after TAC, but remained unchanged across all phases of cardiac pressure overload in Eng$^{+/-}$ mice (Table 1). Echocardiography demonstrated a significant time-dependent reduction in LV fractional shortening (FS %) in WT, but not in Eng$^{+/-}$ mice after TAC. Along with preserved LV function, a significant increase in LV posterior wall thickness (PWT) was noted in both WT and Eng$^{+/-}$ mice after TAC compared to baseline values. However, at ten weeks after TAC, WT mice demonstrated significantly higher LV dilatation and less PWT compared to Eng$^{+/-}$ mice (Table 1). These findings suggest that despite identical degrees of LV pressure overload, reduced Endoglin expression preserved LV function and improved survival across all time points. Notably, compared to WT mice, echocardiographic measures of LV thickness were similar; however, the ability of the LV to generate systolic pressure was significantly higher in Eng$^{+/-}$ mice, suggesting that some component of cardiac remodeling other than cardiac hypertrophy may be altered by reduced Endoglin expression.

Example 3

Reduced Endoglin Expression Attenuates Cardiac Fibrosis

Figures 3A, 3B:
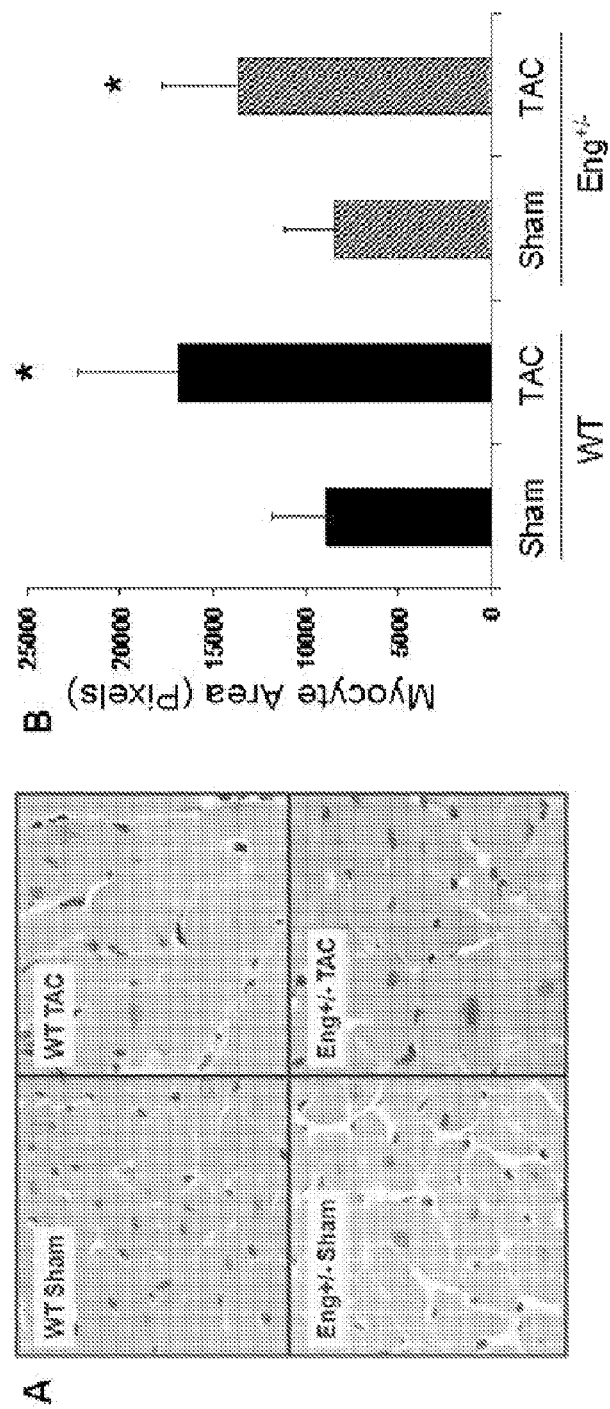
FIGS. 3A-3H are images and graphs showing that reduced Endoglin expression does not affect cardiac hypertrophy but is associated with increased myocardial capillarity.
Figures 3C, 3D, 3E, 3F, 3G, 3H:
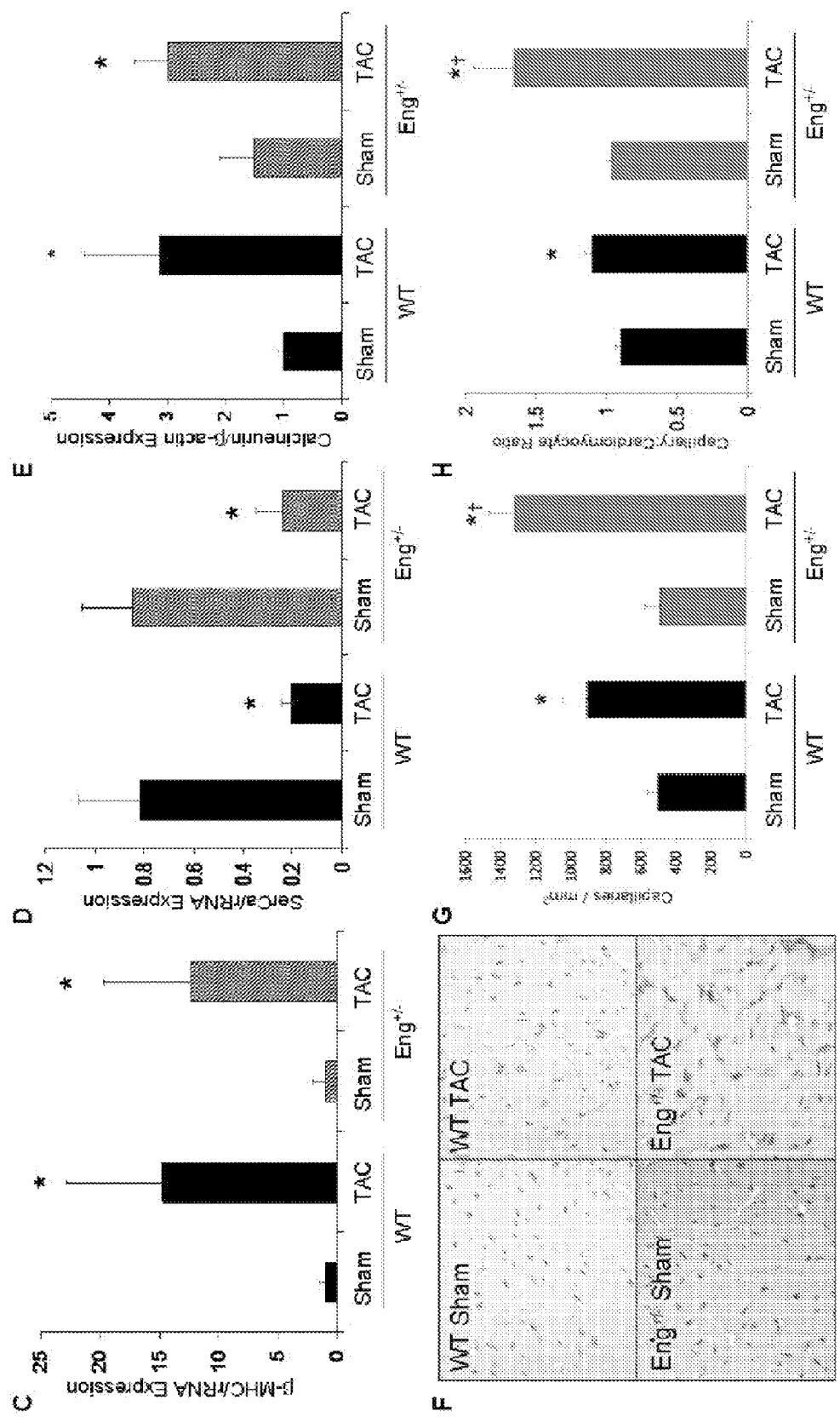
Figures 4A, 4B:
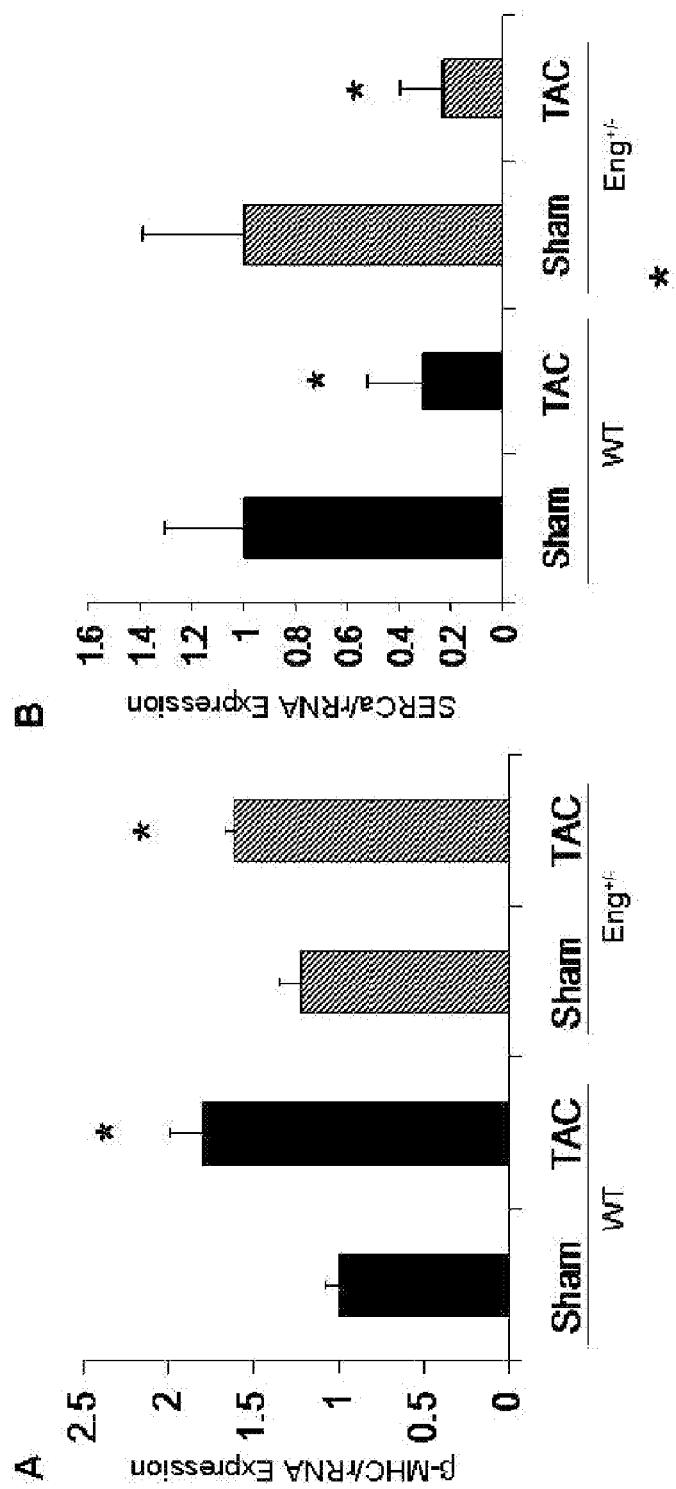
FIGS. 4A-4B are graphs showing similar changes in β-MHC and SERCa in WT and $Eng^{+/-}$ mice after ten weeks of TAC.

To explore the possibility that reduced Endoglin expression attenuates cardiac fibrosis, we examined changes in cardiac hypertrophy. As compared to sham-operated controls, normalized LV mass was significantly increased across all phases of LV pressure overload in both WT and Eng$^{+/-}$ mice. During late-stage heart failure, LV mass was significantly lower in Eng$^{+/-}$ mice compared to WT, likely reflecting the lack of LV dilatation and eccentric remodeling (Table 1). Similarly, myocyte cross-sectional area was significantly increased in both WT and Eng$^{+/-}$ mice after TAC (FIGS. 3A-3B). Expression of fetal genes and proteins known to be activated in heart failure such as β-MHC, SERCa, and calcineurin exhibited similar patterns of expression in both WT and Eng$^{+/-}$ mice after four weeks (FIGS. 3C-3E) and ten weeks of TAC (FIGS. 4A-4B). Next, we examined myocardial capillarity after four weeks of TAC, when both mouse groups manifest similar degrees of LV hypertrophy and observed a significant increase in capillary to cardiomyocyte ratios and total capillary density in WT and Eng$^{+/-}$ mice after TAC. Both measures of myocardial capillarity were higher in Eng$^{+/-}$ compared to WT mice after TAC (FIGS. 3F-3G). Based on the observation that myocyte hypertrophy was similar between groups and that myocardial capillarity was only modestly increased in Eng$^{+/-}$ mice, we next examined changes in cardiac fibrosis.

Figures 6A, 6B, 6C, 6D:
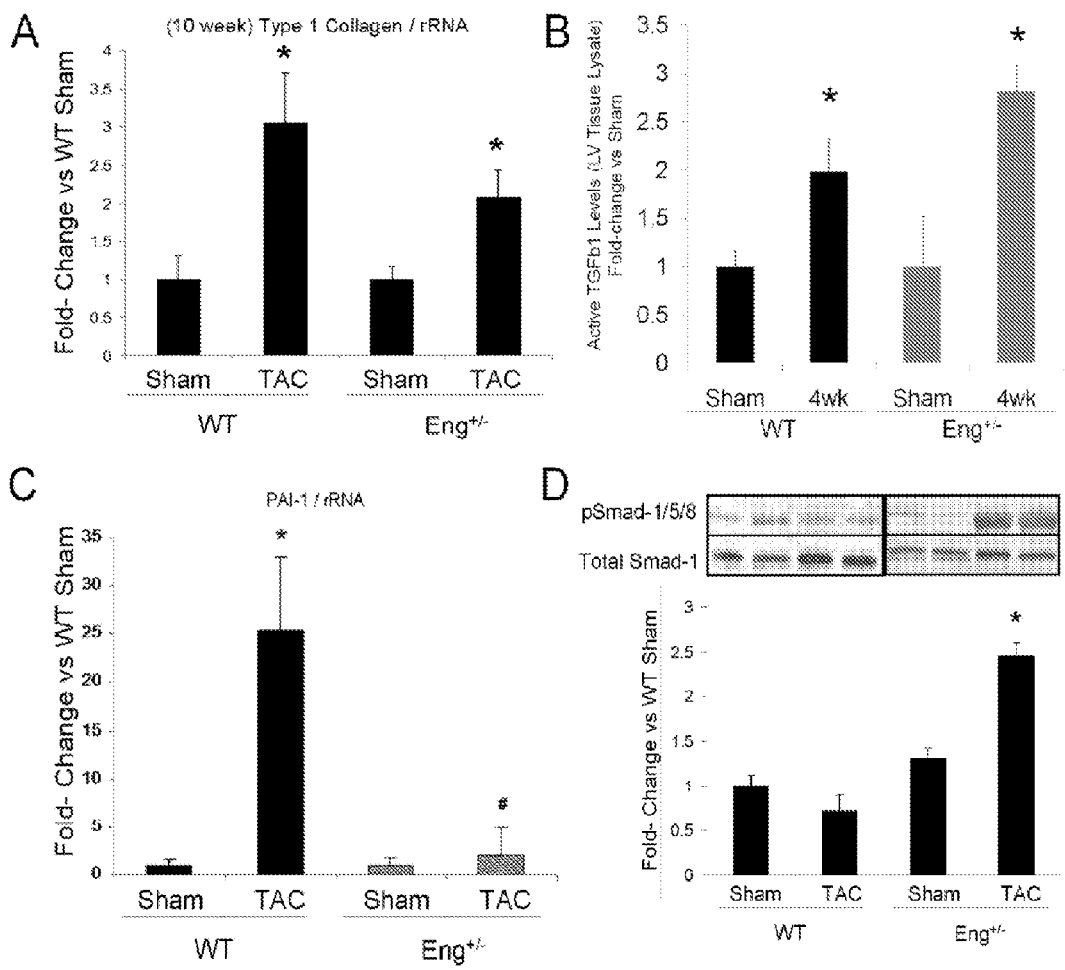
FIGS. 6A-6D are graphs.

Compared to sham-operated controls, quantitation of histologically evident collagen deposition in the LV increased in a time-dependent manner in WT mice, whereas there was no significant change in Eng$^{+/-}$ mice (FIGS. 5A-5B). Type I collagen mRNA (FIG. 5C) and protein expression (FIG. 5D) were similarly increased in WT mice after TAC, while Eng$^{+/-}$ mice exhibited only a small increase in Type 1 collagen expression during the late stages of pressure overload-induced heart failure (FIGS. 5C and 6A). Importantly, increased TGFβ1 mRNA (FIG. 5E) and active TGFβ1 protein (FIG. 6B) expression were observed in the LV of both WT and Eng$^{+/-}$ groups after four weeks of TAC. By ten weeks, TGFβ1 mRNA expression remained elevated in WT TAC compared to WT sham; however, no change in Eng$^{+/-}$ mice was observed compared to sham-operated controls (data not shown). Expression of downstream targets of TGFβ signaling, such as phosphorylated Smad-2/3 (FIG. 5F) and plasminogen activator inhibitor 1 (PAI-1) (FIG. 6C), were significantly increased in WT mice after TAC compared to sham controls. No difference, however, was observed in Eng$^{+/-}$ TAC mice compared to controls. Interestingly, levels of phosphorylated Smad-1/5/8 were not significantly increased in WT mice but were elevated in Eng$^{+/-}$ mice after four weeks of TAC (FIG. 6D). Taken together, these data suggest that reduced Endoglin expression preserves myocyte hypertrophic signaling, while limiting pro-fibrogenic signaling cascades. Furthermore, despite similar increases in TGFβ1 levels, loss of the type III TGFβ1 receptor, Endoglin, was sufficient to attenuate downstream signal transduction, as evidenced by reduced levels of pSmad-2/3 and PAI-1. These in vivo observations led us to explore the dependence of TGFβ1 pro-fibrotic signaling on Endoglin expression in vitro.

Example 4

Membrane-Bound Endoglin is Required for IGFβ1-Induced COL1 Synthesis

Figures 7A, 7B:
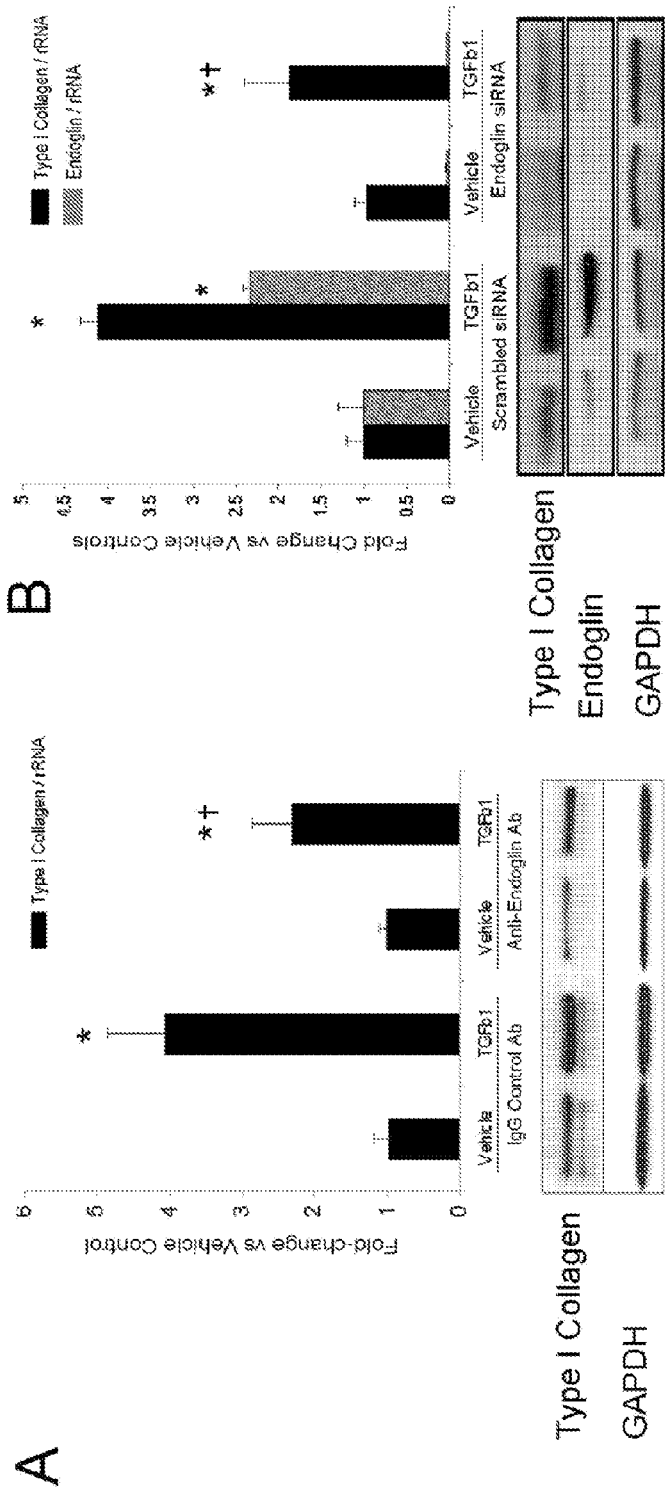
FIGS. 7A-7F are graphs and images showing the opposing roles of mEng and sEng as modulators of TGFβ1-induced type I collagen synthesis in human cardiac fibroblasts (hCF).
Figures 8A, 8B, 8C, 8D:
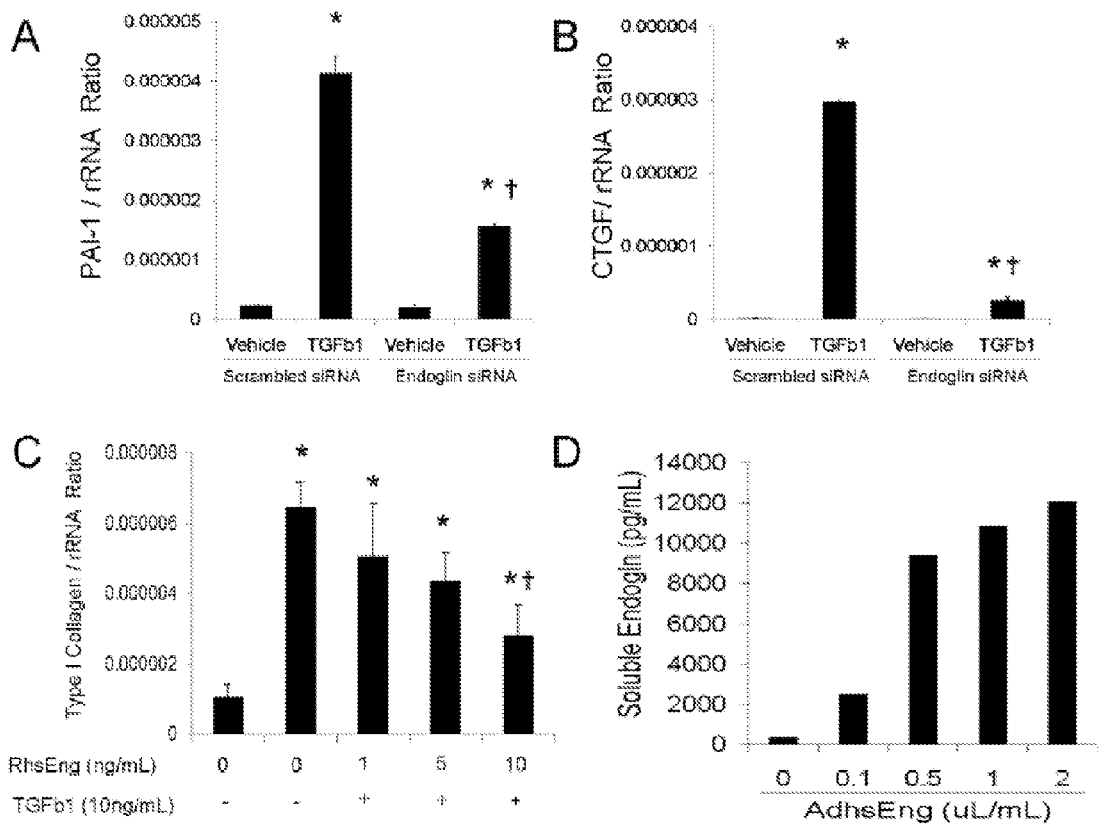
FIGS. 8A-8D are graphs.

We isolated and cultured hCF from fresh tissue samples obtained during cardiac surgery. The role of Endoglin was first examined using a loss-of-function approach. Compared to treatment with an isotype control antibody, pre-treatment with the anti-Endoglin antibody attenuated TGFβ1-induced type I collagen mRNA and protein expression (FIG. 7A). Next, Endoglin expression was silenced using an siRNA approach (siEng) in hCF. Compared to treatment with a scrambled control siRNA, TGFβ1-induced type I collagen mRNA and protein expression were significantly reduced (FIG. 7B). Notably, silencing Endoglin expression also significantly limited TGFβ1-induced expression of PAI-1 and connective tissue growth factor (CTGF) in hCF (FIGS. 8A-8B). These findings highlight the important role that Endoglin plays in regulating TGFβ1 activity in hCF. We next explored whether Endoglin over-expression would promote TGFβ1-induced Type I collagen synthesis.

Example 5

Figure 7C:
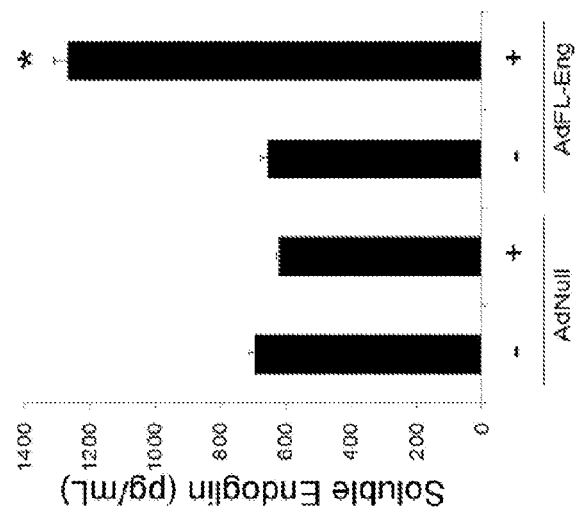
Figure 7D:
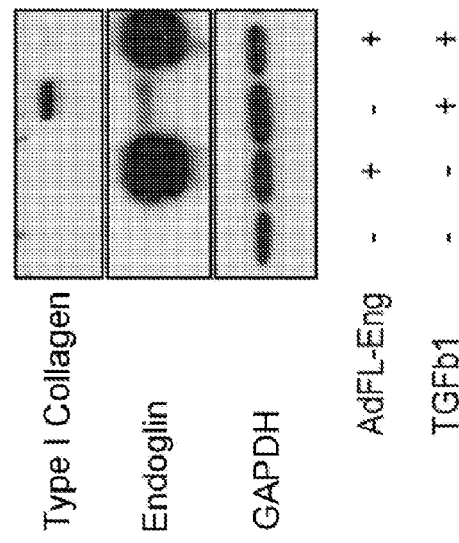
Figures 7E, 7F:
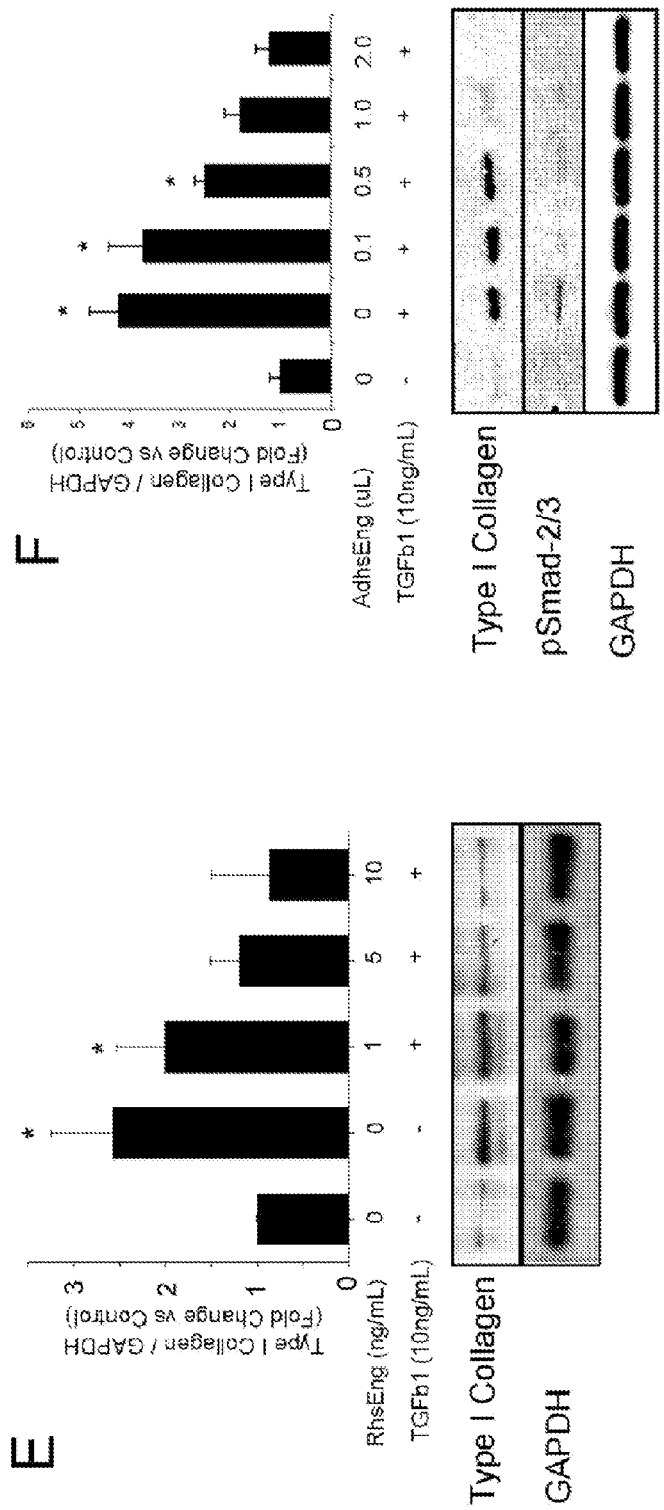

Endoglin Over-Expression Mirrors the Endoglin-Deficient Condition, Likely Due to Increased Soluble Endoglin hCF were transfected with an adenovirus over-expressing full-length Endoglin (Ad-FL-Eng) or a control adenovirus expressing no transgene (AdNull). Interestingly, TGFβ1-induced type I collagen expression was significantly reduced in hCF over-expressing full-length Endoglin (FIG. 7C). To examine why Endoglin over-expression mirrors the findings noted in our loss-of-function studies, we measured levels of sEng in the conditioned media from Ad-FL-Eng transfected hCF and observed significantly higher sEng levels compared to AdNull treated controls (FIG. 7D). To explore whether sEng may regulate TGFβ1-induced type I collagen expression, we pretreated hCF with recombinant human soluble Eng (RhsEng) and observed a dose-dependent decrease in type I collagen protein (FIG. 7E) and mRNA (FIG. 8C) expression compared to vehicle treated controls. To confirm the role of sEng as a negative modulator of TGFβ1 activity, we transfected COS-7 cells with an adenovirus over-expressing human sEng (Ad-hsEng) and confirmed a dose-dependent increase in the level of sEng in culture media (FIG. 8D). Similar to treatment with RhsEng, hCF treated with TGFβ1 in the presence of conditioned media from AdhsEng-transfected COS (AdhsEng-COS) cells also demonstrated a dose-dependent decrease in both TGFβ1-induced pSmad-2/3 expression and Type I collagen expression (FIG. 8F).

Example 6

Figures 9A, 9B, 9C:
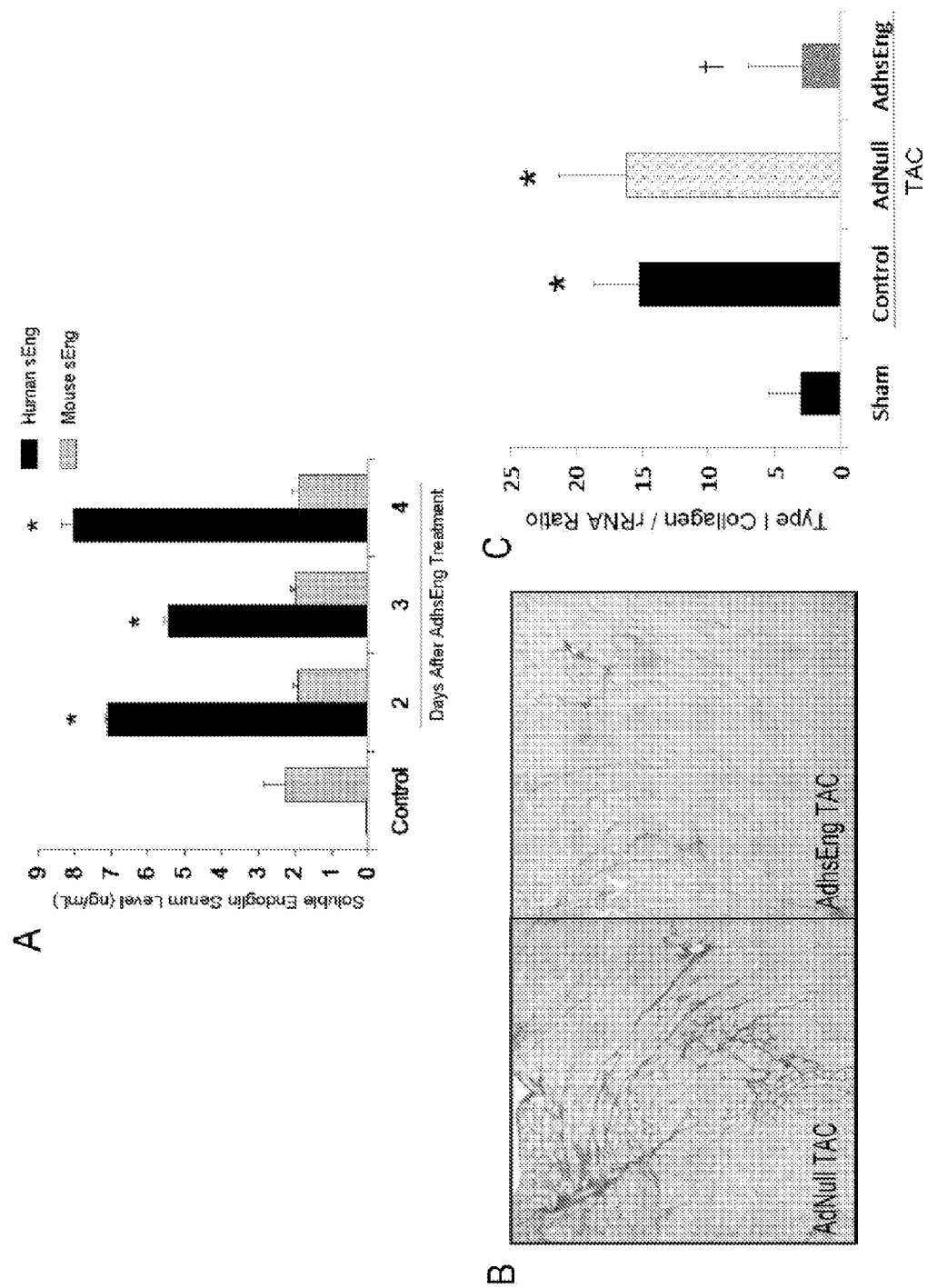
FIGS. 9A-9D are graphs, images, and a schematic diagram showing that over-expressing human sEng limits cardiac fibrosis in vivo.
Figure 9D:
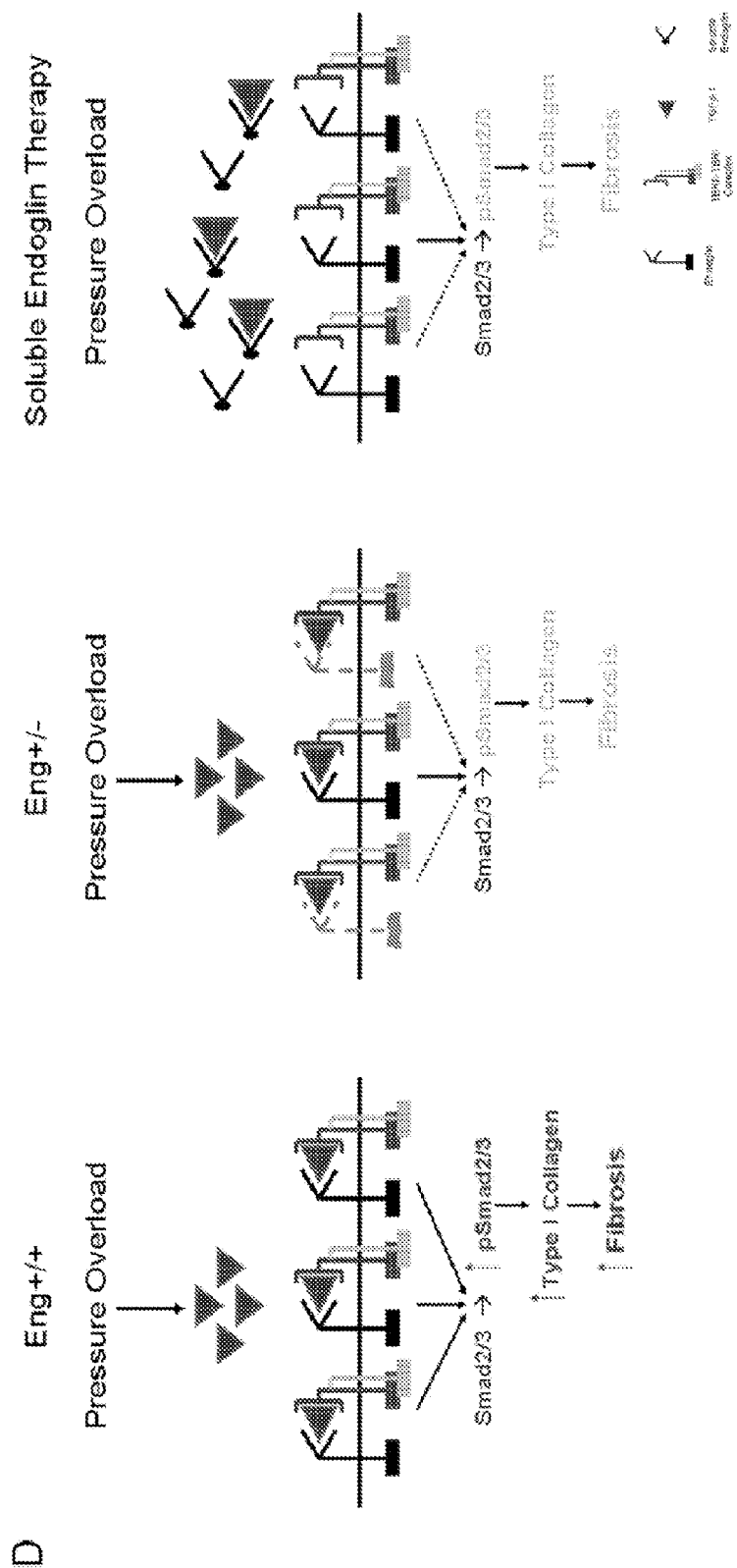

Soluble Endoglin Attenuates Cardiac Fibrosis in Pressure Overload-Induced Heart Failure To explore whether sEng limits cardiac fibrosis in vivo, we first treated WT mice with intravenous injections of AdhsEng and observed significantly increased levels of human sEng in the circulation with no change in basal expression of mouse sEng (FIG. 9A). Next, we treated WT mice with AdhsEng one day prior to induction of cardiac pressure overload. Four weeks after TAC, mice treated with AdhsEng exhibited less cardiac fibrosis (FIG. 9B) and reduced LV expression of Type I collagen (FIG. 9C) compared to AdNull treated controls, thereby indicating sEng as a negative regulator of cardiac fibrosis in pressure overload-induced heart failure.

Example 7

Involvement of Endoglin Signaling in Right Ventricle Pressure Overload

Right ventricular (RV) function is a major determinant of clinical outcomes in pulmonary hypertension (PH). We therefore tested the hypothesis that PH-induced Eng expression augments TGFβ1-activity and fibrosis in the RV, and that blocking endoglin activity limits RV fibrosis in PH.

To explore the functional role of Endoglin in RV remodeling, pulmonary artery constriction (PAC) was performed in male, WT and Endoglin heterozygous ($Eng^{+/-}$) mice. Compared to sham controls, PAC increased RV systolic pressure equally in both WT (21±6 vs. 50±4, p<0.01) and $Eng^{+/-}$ (24±3 vs. 46±9, p<0.01) mice. In WT mice, Eng mRNA and protein expression increased in the RV after 7 days of PAC accompanied by RV fibrosis and hypertrophy. In contrast to WT mice, $Eng^{+/-}$ mice had preserved RV stroke volume (4±1 vs. 7±1, p<0.01) and cardiac output (1.9±0.7 vs. 3.6±0.8 ml/min, p<0.01). Less RV fibrosis was observed in $Eng^{+/-}$ mice, while RV mass was comparable to WT after PAC. Despite similarly increased levels of active TGFβ1 in the RV of WT and Eng+/− mice, levels of pSmad-2/3 and pERK-1/2 were increased in the RV of WT mice, but unchanged in $Eng^{+/-}$ mice after PAC. The dependence of TGFβ1 signaling on Endoglin expression was further tested using a neutralizing anti-endoglin antibody (TRC105; Tracon Pharma). Compared to IgG-treated controls, TRC105 limited RV fibrosis, pSmad-2/3 expression, and Type I Collagen expression in WT mice after PAC. Compared to WT mice, both $Eng^{+/-}$ mice and TRC105-treated mice had improved survival after PAC (60%; n=7/12 vs. 100%; n=8/8 vs. 88%; n=7/8, respectively, p<0.01 for Eng+/− or TRC105 mice vs WT).

Example 8

Materials and Methods

The following materials and methods were used in the examples described above.

Mouse TAC Model

Adult, male, 14-16 week old C57/Bl6 wild-type and $Eng^{+/-}$ mice underwent thoracic aortic constriction (TAC) as previously described (Donaldson et al., Circ. Res. 104:265-75, 2009). At two, four, and ten weeks after TAC, mice were sacrificed, and cardiac tissue and blood were obtained for further analysis by real-time polymerase chain reaction (RT-PCR), immunoblotting, histology, and enzyme linked immunosorbent assays (ELISAs). $Eng^{+/-}$ mice were provided by Michele Letarte, Ph.D. from the University of Toronto.

Physiologic Characterization In Vivo

Transthoracic echocardiography was performed on mice anesthetized with a 10 μl/g intraperitoneal injection of Avidin using a Sonos 5500 echocardiography machine (Hewlett-Packard) equipped with a 15 mHz transducer (Acuson). Parasternal short axis views were obtained through the left ventricle at the papillary muscle level. M-mode tracings were recorded for LA cross-sectional area, LV posterior wall thickness, LV end-diastolic, and end-systolic dimensions. Dimensions were averaged across three cardiac cycles. Hemodynamic assessment was performed at each harvesting time point as previously described by our laboratory using a conductance catheter for measurement of pressure-volume loops (Donaldson et al., Circ. Res. 104: 265-75, 2009).

In Vitro Studies hCF were isolated from myocardial tissue harvested during cardiac surgery at Tufts Medical Center as previously described (Neuss et al., Cell Tissue Res. 286:145-53, 1996). Cells were cultured in fibroblast growth media containing 2% bovine serum albumin (FGM-2, Lonza). Fibroblast phenotype was confirmed using immunostaining for fibroblast specific peptide and discoidin domain receptor 2 (DDR2). All in vitro experiments used cells passaged less than 4 times. hCF were cultured to 80% confluence, then serum-starved for 24 hours. TGFβ1 (Sigma-Aldrich Cat. No. T7039) was prepared as a 50 μg/ml stock solution in 3 μM HCl. Cells were treated with 10 ng/ml TGFβ1 for 30 minutes to evaluate changes in pSmad 2/3 expression or 16-24 hours to study TGFβ1-induced collagen synthesis. RNA, protein lysates, and conditioned media were harvested for subsequent analysis of collagen and Endoglin expression.

Real-Time Quantitative Polymerase Chain Reaction (RT-PCR)

For all cell-based RT-PCR experiments, total RNA was extracted directly using Trizol (Invitrogen). For tissue-based RT-PCR, total RNA was extracted from homogenized tissue samples using Trizol reagent. Total RNA was quantified using a spectrophotometer and 5 μg of extracted RNA was reversed transcribed into cDNA using a High Capacity cDNA Reverse Transcription Kit (Applied Biosystems) with random hexamers for RT-PCR with RT enzyme according to the kit protocol. One tenth of the RT reaction was used as a PCR template using Platinum PFX enzyme (Invitrogen), 0.5 mM magnesium, and the primers for human and mouse Endoglin, type I collagen, TGFβ1, PAI-1, and CTGF. For all RT-PCR experiments, samples were quantified in triplicate using 40 cycles performed at 94° C. for 30 sec, 60° C. for 45 sec, 72° C. for 45 sec using an ABI Prism® 7900 Sequence Detection System.

Immunoblot Analysis (Western Blot)

Tissue homogenates or cultured cells washed with phosphate-buffered saline (PBS) were lysed on ice in RIPA buffer (50 mM Tris/HCl, pH 7.5; 150 mM NaCl; 1% Nonidet P-40; 0.5% deoxycholate; 0.1% SDS) containing protease and phosphatase inhibitors (1 mM PMSF; 1 mM EDTA; 1 µg/ml of leupeptin, aprotinin, and pepstatin A; 1 mM sodium orthovanadate; 50 mM sodium fluoride; 40 mM β-glycerophosphate) and then centrifuged at 18,000 g for 10 min at 4° C. Total protein was quantified using a standard curve (Bio-Rad). Twenty five µg of protein was electrophoresed through 4 to 12% SDS-PAGE gels and then transferred onto Immobilon-P (PVDF) membranes (Millipore, Bedford, Mass.). After blocking overnight, blots were incubated with 1:1000 dilutions of the appropriate primary antibody (see below) followed by incubation with a 1:5,000 dilution of the corresponding horseradish peroxidase-labeled secondary antibody (Amersham). Immunoreactive bands were detected by autoradiography using enhanced chemiluminescence (ECL-Plus; Amersham) and quantified by densitometric analysis using UN-SCAN-IT software (Silk Scientific). Blots may be stripped with a stripping buffer (100 mM 2-mercaptoethanol, 2% SDS, 62.5 mM Tris/HCl, pH 6.7) at 60° C. for 20 min and then re-probed to standardize the amounts of immunoprecipitated protein. Resulting bands were densitometrically analyzed an image software program. Antibodies for human and mouse targeted proteins included Endoglin, COL1, pSmad2/3, pSmad1/5/8, total Smad3, total Smad1, CD-31, and calcineurin.

In Vitro siRNA Protocol

Cardiac fibroblasts were grown to 80% confluence in FGM-2 without antibiotic supplementation. For all siRNA constructs, 50 µM siRNA stock (Ambion) was diluted to a working concentration of 1.0 nM in Optimem (Invitrogen). This working dilution was combined with 21.0 of the cationic lipid transfection reagent Lipofectamine (Invitrogen) diluted in 98 µl of Optimem. After 20 minutes incubation, cultured cells were exposed to the siRNA/Lipofectamine combination. Cells were then treated with human Endoglin siRNA (Ambion Cat. No. 145527). All siRNA experiments were controlled with scrambled siRNA (negative control; Ambion Cat. No. 4390844) and with GAPDH siRNA (positive control; Ambion Cat. No. 4390850). 24-36 hours after transfection, total RNA was isolated and converted to cDNA for RT-PCR analysis as described above. In a separate series, protein lysates was be harvested at 36-48 hours after transfection and analyzed using western blot analysis as described above.

Soluble Endoglin Treatment Protocol In Vitro

Serum-starved cardiac fibroblasts were cultured to 80% confluence, and then treated with recombinant human soluble Endoglin (R&D Systems) derived from the full-length sequence of the extracellular domain of Endoglin for 24 hours. Cells were then stimulated with 10 ng/ml TGFβ1 (Sigma) for an additional 24-48 hours prior to isolation of total RNA and protein lysates for RT-PCR and immunoblot analysis.

Enzyme-Linked Immunosorbent Assays

Commercially available ELISA kits (human Endoglin (R&D Systems, Cat. No. DNDG00); mouse Endoglin (R&D Systems, Cat. No. DY1320)) were used to analyze conditioned media and serum samples from mouse experiments.

Adenoviral Infection of hCF In Vitro

For Endoglin over-expression studies, a first-generation adenovirus expressing the full-length cDNA of human Endoglin (Ad-FL-Eng) was kindly provided by Dr. Calvin Vary of the Maine Medical Center. For over-expression of soluble Endoglin, a first generation adenovirus expressing the full length cDNA for the extracellular domain of human Endoglin (Ad-hs-Eng) was kindly provided by Dr. Ananth Karumanchi (Beth Israel Deaconess Medical Center). Adenoviral transfections in vivo were controlled for using an adenovirus expressing no transgene (AdNull).

Optimal Multiplicity of Infection (MOI)

Cardiac fibroblasts were first grown to 80% confluence on 12-well dishes in 2 ml FGM-2. Virus was thawed on ice and added using a typical MOI dose curve (0, 50, 100, 200, 500, 1000 MOI). Virus-infected cells were incubated for 24 hours at 37° C. Total RNA and protein lysates were extracted for RT-PCR and western blot analysis for human Endoglin.

Over-Expression Protocol In Vitro

Cultured hCF confluent in 100 mm dishes (passage 3) were infected with either an adenovirus expressing no transgene (AdNull) at 20 plaque-forming unit (p.f.u.)/cell in 3 ml of FGM-2 (Lonza). After a 1-hour incubation, cells were rinsed twice with PBS and cultured in 10 ml FGM-2. The culture medium was changed at 24-hour intervals, and the medium plus cells were harvested at 1, 4, 5, 10, 14, 21, and 28 days after infection for immunoblot analysis, ELISA, and RT-PCR. A group of cardiac fibroblasts that were not infected were used as controls for this experiment.

Soluble Endoglin-Conditioned Media Experiment

For conditioned media studies, COS-7 cells were transfected with increasing concentrations of Ad-hs-Eng or AdNull for 24 hours. Conditioned media was isolated and human sEng levels confirmed by ELISA. Conditioned media was then transferred into 12-well dishes containing serum starved hCF, which were then stimulated with TGFβ1 (10 ng/ml).

Other Embodiments

All patents, patent applications, and publications mentioned in this specification are herein incorporated by reference to the same extent as if each independent patent, patent application, or publication was specifically and individually indicated to be incorporated by reference.

The invention claimed is:

1. A method for treating heart failure, left ventricle dysfunction, right ventricle dysfunction, pulmonary hypertension, cardiomyopathy, acute myocardial infarction, or post myocardial infarction in a subject in need thereof, said method comprising administering to said subject a therapeutically effective amount of an antibody or antigen-binding fragment thereof that binds Endoglin and inhibits Endoglin activity.

2. The method of claim 1, wherein said administration results in a reduction of cardiac fibrosis.

3. The method of claim 1, wherein said heart failure is congestive heart failure.

4. The method of claim 1, wherein said heart failure is systolic or diastolic heart failure.

5. The method of claim 1, wherein said subject is suffering or has suffered from coronary artery disease.

6. The method of claim 1, wherein said subject is suffering or has suffered from congenital heart disease, a heart attack, heart valve disease, or an arrhythmia.

7. The method of claim 1, wherein said pulmonary hypertension is adult pulmonary hypertension or pediatric pulmonary hypertension.

8. The method of claim 1, wherein said left or right ventricle dysfunction is asymptomatic left or right ventricle dysfunction, or left or right ventricle dysfunction following myocardial infarction.

9. The method of claim 1, wherein said administration is intravenous, oral, intramuscular, intraarticular, subcutaneous, intraperitoneal, or intralesional.

10. The method of claim 1, wherein said cardiomyopathy is dilated cardiomyopathy.

11. A method for reducing fibrosis in a subject, said method comprising administering to said subject an effective amount of an antibody or antigen-binding fragment thereof that binds Endoglin and inhibits Endoglin activity.

12. The method of claim 11, wherein said subject is suffering from a condition selected from the group consisting of heart failure, left ventricle dysfunction, right ventricle dysfunction, pulmonary hypertension, cardiomyopathy, acute myocardial infarction, or post myocardial infarction.

13. The method of claim 12, wherein said heart failure is congestive heart failure.

14. The method of claim 12, wherein said heart failure is systolic or diastolic heart failure.

15. The method of claim 12, wherein said pulmonary hypertension is adult pulmonary hypertension or pediatric pulmonary hypertension.

16. The method of claim 12, wherein said left or right ventricle dysfunction is asymptomatic left or right ventricle dysfunction, or left or right ventricle dysfunction following myocardial infarction.

17. The method of claim 12, wherein said cardiomyopathy is dilated cardiomyopathy.

18. The method of claim 11, wherein said subject is suffering or has suffered from coronary artery disease.

19. The method of claim 11, wherein said subject is suffering or has suffered from congenital heart disease, a heart attack, heart valve disease, or an arrhythmia.

20. The method of claim 11, wherein said administration is intravenous, oral, intramuscular, intraarticular, subcutaneous, intraperitoneal, or intralesional.

21. The method of claim 11, wherein said fibrosis is cardiac fibrosis.

22. The method of claim 21, wherein said antibody or antigen-binding fragment thereof specifically reduces cardiac fibrosis in the right ventricle.

* * * * *